United States Patent
Aboytes et al.

(10) Patent No.: US 11,517,335 B2
(45) Date of Patent: Dec. 6, 2022

(54) SEALED NEUROVASCULAR EXTENDABLE CATHETER

(71) Applicant: INCEPT, LLC, Lexington, MA (US)

(72) Inventors: Maria Aboytes, Palo Alto, CA (US); Yi Yang, San Francisco, CA (US); Brandon Yee, Oakland, CA (US); Chad C. Roue, San Jose, CA (US); Tiffany C. Suekama, San Jose, CA (US); Ashoor Shahbazi Yourgenlow, San Jose, CA (US); Ryan Taylor Krone, Portland, OR (US)

(73) Assignee: Incept, LLC, Lexington, MA (US)

( * ) Notice: Subject to any disclaimer, the term of this patent is extended or adjusted under 35 U.S.C. 154(b) by 206 days.

(21) Appl. No.: 16/503,899

(22) Filed: Jul. 5, 2019

(65) Prior Publication Data

US 2020/0008820 A1 Jan. 9, 2020

Related U.S. Application Data

(60) Provisional application No. 62/694,796, filed on Jul. 6, 2018.

(51) Int. Cl.
*A61B 17/22* (2006.01)
*A61B 17/00* (2006.01)
(Continued)

(52) U.S. Cl.
CPC .... *A61B 17/22* (2013.01); *A61B 2017/00862* (2013.01); *A61B 2017/22062* (2013.01);
(Continued)

(58) Field of Classification Search
CPC ......... A61B 2017/320028; A61B 2017/32007; A61B 17/320853; A61B 17/32056;
(Continued)

(56) References Cited

U.S. PATENT DOCUMENTS

| 3,605,750 A | 9/1971 | Sheridan et al. |
| 3,884,242 A | 5/1975 | Bazell et al. |

(Continued)

FOREIGN PATENT DOCUMENTS

| CN | 110916768 | 3/2020 |
| DE | 8900059 | 5/1989 |

(Continued)

OTHER PUBLICATIONS

Guidezilla Guide Extension Catheter, Boston Scientific 510k Submission, Feb. 20, 2017.
(Continued)

*Primary Examiner* — Kathleen S Holwerda
*Assistant Examiner* — Lauren Dubose
(74) *Attorney, Agent, or Firm* — Knobbe, Martens, Olson & Bear, LLP

(57) ABSTRACT

A catheter is provided which includes an outer catheter and an extendable inner catheter. A sealing feature is positioned between the inner catheter and the outer catheter to seal the annular gap between the two while allowing axial translation. The seal may be a compliant protrusion surrounding the inner catheter and may have a chevron-shape for facilitating axial translation. The seal may be a one-way valve configured to allow antegrade flushing but prevent retrograde flow. The seal may be squeegee-like flange on the distal tip of the outer catheter. The seal may be an expandable bulge, which may be mechanically expandable or inflatable or which may be a photosensitive or electrosensitive hydrogel. The seal may include a spring that is radially compressed upon translation or rotation of the inner catheter to transiently break the seal. Also provided is a seal for sealing between the catheter and the vasculature.

15 Claims, 22 Drawing Sheets

(51) Int. Cl.
*A61M 25/10* (2013.01)
*A61M 25/00* (2006.01)
*A61L 27/52* (2006.01)

(52) U.S. Cl.
CPC .............. *A61B 2017/22067* (2013.01); *A61B 2017/22079* (2013.01); *A61L 27/52* (2013.01); *A61M 2025/0004* (2013.01); *A61M 2025/1052* (2013.01); *A61M 2205/0272* (2013.01)

(58) Field of Classification Search
CPC .............. A61B 10/04; A61B 2010/045; A61B 10/0283; A61B 17/22; A61B 2017/22067; A61B 2017/22079; A61B 2017/00862; A61B 2017/22062; A61B 17/12109; A61B 17/12131; A61B 17/12136; A61B 17/12172; A61M 2025/1052; A61M 2025/0004; A61M 2025/0175; A61M 25/00; A61M 25/0068
USPC ........................................................ 606/159
See application file for complete search history.

(56) References Cited

U.S. PATENT DOCUMENTS

| | | |
|---|---|---|
| 3,890,976 A | 6/1975 | Bazell et al. |
| 3,965,901 A | 6/1976 | Penny et al. |
| 4,030,503 A | 6/1977 | Clark, III |
| 4,319,580 A | 3/1982 | Colley et al. |
| 4,611,594 A | 9/1986 | Grayhack et al. |
| 4,617,019 A | 10/1986 | Fecht et al. |
| 4,619,274 A | 10/1986 | Morrison et al. |
| 4,628,168 A | 12/1986 | Nebergall et al. |
| 4,762,129 A | 8/1988 | Bonzel |
| 4,762,130 A | 8/1988 | Fogarty et al. |
| 4,767,399 A | 8/1988 | Bollish |
| 4,810,582 A | 3/1989 | Gould et al. |
| 4,844,064 A | 7/1989 | Thimsen et al. |
| 4,898,575 A | 2/1990 | Fischell et al. |
| 4,923,462 A | 5/1990 | Stevens |
| 5,011,488 A | 4/1991 | Ginsburg |
| 5,040,548 A | 8/1991 | Yock |
| 5,103,827 A | 4/1992 | Smith |
| 5,120,323 A | 6/1992 | Shockey et al. |
| 5,217,705 A | 6/1993 | Reno et al. |
| 5,226,909 A | 7/1993 | Evans et al. |
| 5,234,416 A | 8/1993 | Macaulay et al. |
| 5,243,997 A | 9/1993 | Uflacker |
| 5,261,916 A | 11/1993 | Engelson et al. |
| 5,290,247 A | 3/1994 | Crittenden |
| 5,308,327 A | 5/1994 | Heaven et al. |
| 5,328,472 A | 7/1994 | Steinke et al. |
| 5,413,560 A | 5/1995 | Solar |
| 5,417,697 A | 5/1995 | Wilk |
| 5,423,846 A | 6/1995 | Fischell |
| 5,439,445 A | 8/1995 | Kontos |
| 5,441,051 A | 8/1995 | Hileman et al. |
| 5,454,795 A | 10/1995 | Samson |
| 5,466,222 A | 11/1995 | Ressemann et al. |
| 5,474,563 A | 12/1995 | Myler et al. |
| 5,527,292 A | 6/1996 | Adams et al. |
| 5,549,119 A | 8/1996 | Solar |
| 5,569,178 A | 10/1996 | Henley |
| 5,569,277 A | 10/1996 | Evans et al. |
| 5,591,187 A | 1/1997 | Dekel |
| 5,643,254 A | 7/1997 | Scheldrup et al. |
| 5,658,263 A | 8/1997 | Dang et al. |
| 5,662,622 A | 9/1997 | Gore et al. |
| 5,690,613 A | 11/1997 | Verbeek |
| 5,695,483 A | 12/1997 | Samson |
| 5,702,373 A | 12/1997 | Samson |
| 5,766,191 A | 6/1998 | Trerotola |
| 5,776,141 A | 7/1998 | Klein et al. |
| 5,827,242 A | 10/1998 | Follmer |
| 5,843,103 A | 12/1998 | Wulfman |
| 5,873,882 A | 2/1999 | Straub et al. |
| 5,876,414 A | 3/1999 | Straub |
| 5,885,209 A | 3/1999 | Green |
| 5,891,114 A | 4/1999 | Chien et al. |
| 5,895,398 A | 4/1999 | Wensel |
| 5,899,892 A | 5/1999 | Mortier et al. |
| 5,916,192 A | 6/1999 | Nita et al. |
| 5,935,112 A | 8/1999 | Stevens |
| 5,951,539 A | 9/1999 | Nita |
| 6,007,530 A | 12/1999 | Dornhofer et al. |
| 6,056,837 A | 5/2000 | Lieber et al. |
| 6,059,745 A | 5/2000 | Gelbfish |
| 6,090,118 A | 7/2000 | McGuckin, Jr. |
| 6,159,230 A | 12/2000 | Samuels |
| 6,165,163 A | 12/2000 | Chien et al. |
| 6,165,199 A | 12/2000 | Barbut |
| 6,171,295 B1 | 1/2001 | Garabedian et al. |
| 6,179,859 B1 | 1/2001 | Bates |
| 6,197,014 B1 | 3/2001 | Samson et al. |
| 6,206,852 B1 | 3/2001 | Lee |
| 6,217,557 B1 | 4/2001 | Hakansson et al. |
| 6,221,038 B1 | 4/2001 | Brisken |
| 6,228,046 B1 | 5/2001 | Brisken |
| 6,258,052 B1 | 7/2001 | Milo |
| 6,267,783 B1 | 7/2001 | Letendre et al. |
| 6,285,903 B1 | 9/2001 | Rosenthal |
| 6,355,027 B1 | 3/2002 | Le et al. |
| 6,394,976 B1 | 5/2002 | Winston et al. |
| 6,451,036 B1 | 6/2002 | Heitzmann |
| 6,451,005 B1 | 9/2002 | Saitou et al. |
| 6,458,139 B1 | 10/2002 | Palmer et al. |
| 6,468,219 B1 | 10/2002 | Njemanze |
| 6,482,217 B1 | 11/2002 | Pintor et al. |
| 6,511,492 B1 | 1/2003 | Rosenbluth |
| 6,524,303 B1 | 2/2003 | Garibaldi et al. |
| 6,520,934 B1 | 3/2003 | Lee |
| 6,533,751 B2 | 3/2003 | Cragg |
| 6,554,820 B1 | 4/2003 | Wendlandt |
| 6,554,827 B2 | 4/2003 | Chandrasekaran et al. |
| 6,558,377 B2 | 5/2003 | Lee et al. |
| 6,569,148 B2 | 5/2003 | Bagaoisan et al. |
| 6,579,246 B2 | 6/2003 | Jacobsen et al. |
| 6,582,440 B1 | 6/2003 | Brumbach |
| 6,591,472 B1 | 7/2003 | Noone et al. |
| 6,638,268 B2 | 10/2003 | Niazi |
| 6,666,874 B2 | 12/2003 | Heitzmann |
| 6,669,670 B1 | 12/2003 | Muni et al. |
| 6,719,717 B1 | 4/2004 | Johnson et al. |
| 6,776,770 B1 | 8/2004 | Trerotola |
| 6,824,550 B1 | 11/2004 | Pintor et al. |
| 6,977,068 B1 | 12/2005 | Nair et al. |
| 7,004,954 B1 | 2/2006 | Voss et al. |
| 7,008,434 B2 | 3/2006 | Kurz et al. |
| 7,029,482 B1 | 4/2006 | Vargas |
| 7,037,267 B1 | 5/2006 | Lipson et al. |
| 7,104,979 B2 | 9/2006 | Jansen et al. |
| 7,112,298 B2 | 9/2006 | Kampa et al. |
| 7,172,620 B2 | 2/2007 | Gilson |
| 7,175,653 B2 | 2/2007 | Gaber |
| 7,207,980 B2 | 4/2007 | Christian et al. |
| 7,223,274 B2 | 5/2007 | Vargas |
| 7,229,461 B2 | 6/2007 | Chin et al. |
| 7,232,452 B2 | 6/2007 | Adams et al. |
| 7,235,088 B2 | 6/2007 | Pintor et al. |
| 7,306,585 B2 | 12/2007 | Ross |
| 7,309,334 B2 | 12/2007 | von Hoffmann |
| 7,335,216 B2 | 2/2008 | Bender |
| 7,491,210 B2 | 2/2009 | Dubrul et al. |
| 7,507,229 B2 | 3/2009 | Hewitt et al. |
| 7,537,568 B2 | 5/2009 | Moehring |
| 7,558,622 B2 | 7/2009 | Tran |
| 7,601,138 B2 | 10/2009 | Goebel et al. |
| 7,678,100 B2 | 3/2010 | Chin et al. |
| 7,713,227 B2 | 5/2010 | Wholey et al. |
| 7,763,196 B2 | 7/2010 | Goebel et al. |
| 7,771,358 B2 | 8/2010 | Moehring et al. |
| 7,803,136 B2 | 9/2010 | Schatz |
| 7,837,692 B2 | 11/2010 | Mulholland et al. |

(56) References Cited

U.S. PATENT DOCUMENTS

| | | |
|---|---|---|
| 7,842,055 B2 | 11/2010 | Pintor et al. |
| 7,850,623 B2 | 12/2010 | Griffin |
| 7,905,891 B2 | 3/2011 | Self |
| 7,931,659 B2 | 4/2011 | Bose et al. |
| 7,938,820 B2 | 5/2011 | Webster et al. |
| 7,988,646 B2 | 8/2011 | Taber |
| 8,021,351 B2 | 9/2011 | Boldenow et al. |
| 8,048,032 B2 | 11/2011 | Root et al. |
| 8,057,497 B1 | 11/2011 | Raju et al. |
| 8,062,316 B2 | 11/2011 | Patel |
| 8,070,694 B2 | 12/2011 | Galdonik et al. |
| 8,084,246 B2 | 12/2011 | Hoon et al. |
| 8,114,106 B2 | 2/2012 | Straub |
| 8,142,413 B2 | 3/2012 | Root et al. |
| 8,114,032 B2 | 4/2012 | Ferry et al. |
| 8,157,792 B2 | 4/2012 | Dolliver et al. |
| 8,211,023 B2 | 7/2012 | Swan et al. |
| 8,235,968 B2 | 8/2012 | Tremaglio |
| 8,246,641 B2 | 8/2012 | Osborne et al. |
| 8,292,850 B2 | 10/2012 | Root et al. |
| 8,298,591 B2 | 10/2012 | Srivastava et al. |
| 8,361,095 B2 | 1/2013 | Osborne |
| 8,366,735 B2 | 2/2013 | Bose et al. |
| 8,382,739 B2 | 2/2013 | Walak et al. |
| 8,394,078 B2 | 3/2013 | Torrance et al. |
| 8,403,912 B2 | 3/2013 | McFerran et al. |
| 8,460,312 B2 | 6/2013 | Bose et al. |
| 8,485,969 B2 | 7/2013 | Grayzel et al. |
| 8,517,955 B2 | 8/2013 | Keast |
| 8,535,293 B2 | 9/2013 | Faherty et al. |
| 8,568,432 B2 | 10/2013 | Straub |
| 8,608,754 B2 | 12/2013 | Wensel et al. |
| 8,609,426 B2 | 12/2013 | Silver |
| 8,663,259 B2 | 3/2014 | Levine et al. |
| 8,682,411 B2 | 3/2014 | Kassab et al. |
| 8,684,963 B2 | 4/2014 | Qiu et al. |
| 8,696,698 B2 | 4/2014 | Chomas |
| 8,702,680 B2 | 4/2014 | Jimenez et al. |
| 8,725,249 B2 | 5/2014 | Bar-Yoseph et al. |
| 8,734,374 B2 | 5/2014 | Aklog et al. |
| 8,758,325 B2 | 6/2014 | Webster et al. |
| 8,764,779 B2 | 7/2014 | Levine et al. |
| 8,814,892 B2 | 8/2014 | Galdonik et al. |
| 8,864,792 B2 | 10/2014 | Eckhouse |
| 8,876,854 B2 | 11/2014 | Christiansen et al. |
| 8,900,257 B2 | 12/2014 | Straub et al. |
| 8,932,320 B1 | 1/2015 | Janardhan et al. |
| RE45,380 E | 2/2015 | Root et al. |
| 8,968,383 B1 | 3/2015 | Johnson et al. |
| 8,974,411 B2 | 3/2015 | McKinnon |
| 8,992,506 B2 | 3/2015 | Gulachenski |
| 8,996,095 B2 | 3/2015 | Anderson et al. |
| 8,998,946 B2 | 4/2015 | Morero et al. |
| 9,014,786 B2 | 4/2015 | Carmeli et al. |
| 9,017,309 B2 | 4/2015 | Tanikawa et al. |
| 9,023,070 B2 | 5/2015 | Levine et al. |
| 9,039,715 B2 | 5/2015 | Diamant et al. |
| 9,079,000 B2 | 7/2015 | Hanson et al. |
| 9,107,691 B2 | 8/2015 | Fojtik |
| 9,119,625 B2 | 9/2015 | Bachman et al. |
| 9,119,656 B2 | 9/2015 | Bose et al. |
| 9,144,383 B2 | 9/2015 | Zharov |
| 9,144,662 B2 | 9/2015 | DiCaprio et al. |
| RE45,760 E | 10/2015 | Root et al. |
| RE45,776 E | 10/2015 | Root et al. |
| 9,199,064 B2 | 12/2015 | Morero |
| 9,238,124 B2 | 1/2016 | Grayzel et al. |
| 9,241,699 B1 | 1/2016 | Kume et al. |
| 9,259,215 B2 | 2/2016 | Chou et al. |
| 9,259,228 B2 | 2/2016 | Cruise et al. |
| 9,265,512 B2 | 2/2016 | Garrison et al. |
| 9,278,201 B2 | 3/2016 | Rapaport et al. |
| 9,282,992 B2 | 3/2016 | Levine et al. |
| 9,295,817 B2 | 3/2016 | Chang |
| 9,314,268 B2 | 4/2016 | Cahill |
| 9,345,856 B2 * | 5/2016 | Witte .................. A61M 25/04 |
| 9,351,993 B2 | 5/2016 | Cruise et al. |
| 9,370,639 B2 | 6/2016 | Plassman et al. |
| 9,375,223 B2 | 6/2016 | Wallace |
| 9,381,278 B2 | 7/2016 | Constant et al. |
| 9,399,118 B2 | 7/2016 | Kume et al. |
| RE46,116 E | 8/2016 | Root et al. |
| 9,408,916 B2 | 8/2016 | Cruise et al. |
| 9,414,819 B2 | 8/2016 | Fitz et al. |
| 9,421,328 B2 | 8/2016 | Brueckner et al. |
| 9,439,791 B2 | 9/2016 | Vong et al. |
| 9,440,018 B2 | 9/2016 | Levin et al. |
| 9,446,216 B2 | 9/2016 | Olesky et al. |
| 9,451,884 B2 | 9/2016 | Palovich |
| 9,451,963 B2 | 9/2016 | Cruise et al. |
| 9,463,006 B2 | 10/2016 | Forde et al. |
| 9,480,813 B2 | 11/2016 | Fukuoka et al. |
| 9,486,221 B2 | 11/2016 | Cruise et al. |
| 9,492,637 B2 | 11/2016 | Garrison et al. |
| 9,504,476 B2 | 11/2016 | Gulachenski |
| 9,510,855 B2 | 12/2016 | Rapaport et al. |
| 9,526,504 B2 | 12/2016 | Chang |
| 9,526,505 B2 | 12/2016 | Marks et al. |
| 9,532,792 B2 | 1/2017 | Galdonik et al. |
| 9,533,344 B2 | 1/2017 | Monetti et al. |
| 9,539,022 B2 | 1/2017 | Bowman |
| 9,539,122 B2 | 1/2017 | Burke et al. |
| 9,546,236 B2 | 1/2017 | Cruise et al. |
| 9,561,121 B2 | 2/2017 | Sudin et al. |
| 9,561,125 B2 | 2/2017 | Bowman et al. |
| 9,561,345 B2 | 2/2017 | Garrison et al. |
| 9,597,101 B2 | 3/2017 | Galdonik et al. |
| 9,597,212 B2 | 3/2017 | Thompson et al. |
| 9,615,832 B2 | 3/2017 | Bose et al. |
| 9,622,753 B2 | 4/2017 | Cox |
| 9,623,228 B2 | 4/2017 | Ryan et al. |
| 9,655,633 B2 | 5/2017 | Leynov et al. |
| 9,655,755 B2 | 5/2017 | Chou et al. |
| 9,655,989 B2 | 5/2017 | Cruise et al. |
| 9,662,118 B2 | 5/2017 | Chang |
| 9,662,129 B2 | 5/2017 | Galdonik et al. |
| 9,662,480 B2 | 5/2017 | Kume et al. |
| 9,669,183 B2 | 6/2017 | Chang |
| 9,669,191 B2 | 6/2017 | Chou et al. |
| 9,681,882 B2 | 6/2017 | Garrison et al. |
| 9,688,788 B2 | 6/2017 | Plotkin et al. |
| 9,693,789 B2 | 7/2017 | Garrison et al. |
| 9,693,852 B2 | 7/2017 | Lam et al. |
| 9,707,380 B2 | 7/2017 | Qiu et al. |
| 9,717,500 B2 | 8/2017 | Tieu et al. |
| 9,724,103 B2 | 8/2017 | Cruise et al. |
| 9,724,491 B2 | 8/2017 | Solar et al. |
| 9,764,111 B2 | 9/2017 | Gulachenski |
| 9,770,251 B2 | 9/2017 | Bowman et al. |
| 9,789,242 B2 | 9/2017 | Criado et al. |
| 9,775,730 B1 | 10/2017 | Waltzman |
| 9,789,283 B2 | 10/2017 | Richter et al. |
| 9,801,643 B2 | 10/2017 | Hansen et al. |
| 9,803,043 B2 | 10/2017 | Cruise et al. |
| 9,808,610 B2 | 11/2017 | Li et al. |
| 9,820,761 B2 | 11/2017 | Garrison et al. |
| 9,827,047 B2 | 11/2017 | Fudaba et al. |
| 9,855,072 B2 | 1/2018 | Moberg et al. |
| 9,861,783 B2 | 1/2018 | Garrison et al. |
| 9,877,731 B2 | 1/2018 | Cruise et al. |
| 9,907,880 B2 | 1/2018 | Cruise et al. |
| 9,883,885 B2 | 2/2018 | Hendrick et al. |
| 9,913,960 B2 | 3/2018 | Blanchard et al. |
| 9,987,028 B2 | 6/2018 | Lowinger et al. |
| 9,999,355 B2 | 6/2018 | Kirenko |
| 10,010,698 B2 | 7/2018 | Watanabe et al. |
| 10,028,854 B2 | 7/2018 | Tatalovich et al. |
| 10,039,906 B2 | 8/2018 | Kume et al. |
| 10,070,878 B2 | 9/2018 | Ma |
| 10,086,169 B2 | 10/2018 | Grayzel et al. |
| 10,105,154 B1 | 10/2018 | Green |
| 10,179,224 B2 | 1/2019 | Yang et al. |
| 10,183,145 B2 | 1/2019 | Yang et al. |
| 10,183,146 B2 | 1/2019 | Yang et al. |

(56) References Cited

U.S. PATENT DOCUMENTS

| | | |
|---|---|---|
| 10,183,147 B2 | 1/2019 | Yang et al. |
| 10,207,077 B2 | 2/2019 | Griggin et al. |
| 10,213,582 B2 | 2/2019 | Garrison et al. |
| 10,226,277 B2 | 3/2019 | Smith et al. |
| 10,238,833 B2 | 3/2019 | Christian et al. |
| 10,258,452 B2 | 4/2019 | Eckhouse et al. |
| 10,265,086 B2 | 4/2019 | Vale et al. |
| 10,271,864 B2 | 4/2019 | Greenhalgh et al. |
| 10,278,678 B2 | 5/2019 | Peliks |
| 10,278,816 B2 | 5/2019 | Miller et al. |
| 10,327,790 B2 | 6/2019 | Garrison et al. |
| 10,335,186 B2 | 7/2019 | Rosenbluth et al. |
| 10,342,570 B2 | 7/2019 | Richter et al. |
| 10,383,691 B2 | 8/2019 | Hendrick et al. |
| 10,384,034 B2 | 8/2019 | Garrison et al. |
| 10,420,581 B2 | 9/2019 | Hehrlein et al. |
| 10,441,745 B2 | 10/2019 | Yang et al. |
| 10,456,552 B2 | 10/2019 | Goyal |
| 10,471,233 B2 | 11/2019 | Garrison et al. |
| 10,524,814 B2 | 1/2020 | Chang et al. |
| 10,531,883 B1 | 1/2020 | Deville et al. |
| 10,537,706 B2 | 1/2020 | Kanemasa et al. |
| 10,569,049 B2 | 2/2020 | Garrison et al. |
| 10,610,668 B2 | 4/2020 | Burkholz et al. |
| 10,646,239 B2 | 5/2020 | Garrison et al. |
| 10,653,434 B1 | 5/2020 | Yang et al. |
| 10,668,192 B2 | 6/2020 | Raney et al. |
| 10,695,159 B2 | 6/2020 | Hauser |
| 10,716,880 B2 | 7/2020 | Culbert et al. |
| 10,716,915 B2 | 7/2020 | Ogle et al. |
| 10,722,251 B2 | 7/2020 | Garrison et al. |
| 10,722,253 B2 | 7/2020 | Deville et al. |
| 10,722,683 B2 | 7/2020 | Solar et al. |
| 10,743,893 B2 | 8/2020 | Garrison et al. |
| 10,786,270 B2 | 9/2020 | Yang |
| 10,856,898 B2 | 12/2020 | Matsushita et al. |
| 10,888,280 B2 | 1/2021 | Newberry |
| 10,905,850 B2 | 2/2021 | Christian et al. |
| 11,020,030 B2 | 6/2021 | Tao et al. |
| 11,065,018 B2 | 7/2021 | Buck et al. |
| 11,076,876 B2 | 8/2021 | Vale |
| 11,197,683 B1 | 12/2021 | Teigen et al. |
| 11,207,096 B2 | 12/2021 | To et al. |
| 11,207,497 B1 | 12/2021 | Yee et al. |
| 2001/0031980 A1 | 10/2001 | Wensel et al. |
| 2001/0031981 A1 | 10/2001 | Evans |
| 2001/0049486 A1 | 12/2001 | Evans et al. |
| 2002/0016565 A1 | 2/2002 | Zadno-Azizi et al. |
| 2002/0026145 A1 | 2/2002 | Bagaoisan et al. |
| 2002/0074276 A1 | 6/2002 | Nakashima |
| 2002/0091372 A1 | 7/2002 | Cragg |
| 2002/0156459 A1 | 10/2002 | Ye et al. |
| 2002/0156460 A1 | 10/2002 | Ye |
| 2002/0169467 A1 | 11/2002 | Heitzmann |
| 2002/0177899 A1 | 11/2002 | Eum et al. |
| 2002/0188314 A1 | 12/2002 | Anderson et al. |
| 2003/0088266 A1 | 5/2003 | Bowlin |
| 2003/0135193 A1 | 7/2003 | Hilgers et al. |
| 2003/0135198 A1 | 7/2003 | Berhow et al. |
| 2003/0153874 A1 | 8/2003 | Tal |
| 2003/0195467 A1 | 10/2003 | Mickley |
| 2003/0195546 A1 | 10/2003 | Solar et al. |
| 2003/0225336 A1 | 12/2003 | Callister et al. |
| 2004/0010280 A1 | 1/2004 | Adams et al. |
| 2004/0059290 A1 | 3/2004 | Palasis |
| 2004/0138693 A1 | 7/2004 | Eskuri |
| 2004/0153049 A1 | 8/2004 | Hewitt et al. |
| 2004/0199201 A1 | 10/2004 | Kellett |
| 2004/0236215 A1 | 11/2004 | Mihara et al. |
| 2004/0243102 A1 | 12/2004 | Berg et al. |
| 2005/0004523 A1 | 1/2005 | Osborne et al. |
| 2005/0004553 A1 | 1/2005 | Douk |
| 2005/0021002 A1 | 1/2005 | Deckman et al. |
| 2005/0055047 A1 | 3/2005 | Greenhalgh |
| 2005/0059957 A1 | 3/2005 | Campbell |
| 2005/0080400 A1 | 4/2005 | Corcoran et al. |
| 2005/0103332 A1 | 5/2005 | Gingles et al. |
| 2005/0137680 A1 | 6/2005 | Ortiz et al. |
| 2005/0182386 A1 | 8/2005 | Aggerholm |
| 2006/0030835 A1 | 2/2006 | Sherman et al. |
| 2006/0064036 A1 | 3/2006 | Osborne et al. |
| 2006/0095062 A1 | 5/2006 | Stephens |
| 2006/0100530 A1 | 5/2006 | Kliot et al. |
| 2006/0111649 A1 | 5/2006 | Zhou |
| 2006/0124212 A1 | 6/2006 | Zhou |
| 2006/0149355 A1 | 7/2006 | Mitelberg et al. |
| 2006/0217664 A1 | 9/2006 | Hattler et al. |
| 2006/0247755 A1 | 11/2006 | Pal et al. |
| 2006/0264759 A1 | 11/2006 | Moehring et al. |
| 2007/0016132 A1 | 1/2007 | Oepen et al. |
| 2007/0043333 A1 | 2/2007 | Kampa et al. |
| 2007/0060888 A1 | 3/2007 | Goff et al. |
| 2007/0185521 A1 | 8/2007 | Bui et al. |
| 2007/0197956 A1 | 8/2007 | Le et al. |
| 2007/0225614 A1 | 9/2007 | Naghavi et al. |
| 2008/0064984 A1 | 3/2008 | Pflueger et al. |
| 2008/0086110 A1 | 4/2008 | Galdonik et al. |
| 2008/0097251 A1 | 4/2008 | Babaev et al. |
| 2008/0188928 A1 | 8/2008 | Salahieh et al. |
| 2008/0234715 A1 | 9/2008 | Pesce |
| 2008/0262350 A1 | 10/2008 | Unger |
| 2008/0300544 A1 | 12/2008 | Palm et al. |
| 2008/0312639 A1 | 12/2008 | Weber |
| 2009/0030400 A1 | 1/2009 | Bose et al. |
| 2009/0043330 A1 | 2/2009 | To |
| 2009/0182370 A1 | 7/2009 | Volobuyev et al. |
| 2009/0187143 A1 | 7/2009 | Vreeman |
| 2009/0209857 A1 | 8/2009 | Secretain et al. |
| 2009/0210048 A1 | 8/2009 | Amplatz et al. |
| 2009/0227992 A1 | 9/2009 | Nir et al. |
| 2009/0234321 A1 | 9/2009 | Shapland et al. |
| 2009/0264865 A1 | 10/2009 | Kawai |
| 2009/0270888 A1 | 10/2009 | Patel |
| 2009/0275974 A1 | 11/2009 | Marchand et al. |
| 2009/0312699 A1 | 12/2009 | Pudelko |
| 2010/0030256 A1 | 2/2010 | Dubrul et al. |
| 2010/0049168 A1 | 2/2010 | Parker et al. |
| 2010/0057051 A1 | 3/2010 | Howat et al. |
| 2010/0114017 A1 | 5/2010 | Lenker et al. |
| 2010/0125253 A1 | 5/2010 | Olson et al. |
| 2010/0217235 A1 | 8/2010 | Thorstenson et al. |
| 2010/0217276 A1 | 8/2010 | Garrison et al. |
| 2010/0312141 A1 | 12/2010 | Keast et al. |
| 2011/0009875 A1 | 1/2011 | Grandfield et al. |
| 2011/0034986 A1 | 2/2011 | Chou |
| 2011/0054504 A1 | 3/2011 | Porter |
| 2011/0082373 A1 | 4/2011 | Gurley et al. |
| 2011/0106200 A1 | 5/2011 | Ziegler |
| 2011/0137399 A1 | 6/2011 | Chomas et al. |
| 2011/0152998 A1 | 6/2011 | Berez et al. |
| 2011/0172700 A1 | 7/2011 | Bose et al. |
| 2011/0178418 A1 | 7/2011 | Avidor et al. |
| 2011/0230859 A1 | 9/2011 | Galdonik et al. |
| 2011/0238041 A1 | 9/2011 | Lim et al. |
| 2011/0295217 A1 | 12/2011 | Tanaka et al. |
| 2012/0040858 A1 | 2/2012 | Ford et al. |
| 2012/0041474 A1 | 2/2012 | Eckhouse |
| 2012/0065479 A1 | 3/2012 | Lahiji et al. |
| 2012/0065490 A1 | 3/2012 | Zharov et al. |
| 2012/0078140 A1 | 3/2012 | Nita |
| 2012/0083868 A1 | 4/2012 | Shrivastava et al. |
| 2012/0123327 A1 | 5/2012 | Miller |
| 2012/0143237 A1 | 6/2012 | Cam et al. |
| 2012/0150147 A1 | 6/2012 | Leynov et al. |
| 2012/0290067 A1 | 11/2012 | Cam et al. |
| 2012/0330196 A1 | 12/2012 | Nita |
| 2013/0006225 A1 | 1/2013 | Cucin |
| 2013/0018318 A1 | 1/2013 | Ravichandran et al. |
| 2013/0018359 A1 | 1/2013 | Coyle |
| 2013/0035628 A1 | 2/2013 | Garrison et al. |
| 2013/0046285 A1 | 2/2013 | Griffin et al. |
| 2013/0046374 A1 | 2/2013 | Jones-McMeans |
| 2013/0116701 A1 | 5/2013 | Wang et al. |
| 2013/0131641 A1 | 5/2013 | Jimenez et al. |

(56) References Cited

U.S. PATENT DOCUMENTS

| | | |
|---|---|---|
| 2013/0131710 A1 | 5/2013 | Carmeli |
| 2013/0158578 A1 | 6/2013 | Ghodke et al. |
| 2014/0025043 A1 | 1/2014 | Wang et al. |
| 2014/0074144 A1 | 3/2014 | Shrivastava et al. |
| 2014/0114287 A1 | 4/2014 | Beasley et al. |
| 2014/0121746 A1 | 5/2014 | Kusleika et al. |
| 2014/0155932 A1 | 6/2014 | Bose et al. |
| 2014/0155980 A1 | 6/2014 | Turjman et al. |
| 2014/0163367 A1 | 6/2014 | Eskuri |
| 2014/0228808 A1 | 8/2014 | Webster et al. |
| 2014/0243882 A1 | 8/2014 | Ma |
| 2014/0249508 A1 | 9/2014 | Wang et al. |
| 2014/0271718 A1 | 9/2014 | Alvarez |
| 2014/0273920 A1 | 9/2014 | Smith |
| 2014/0275832 A1 | 9/2014 | Muehlsteff et al. |
| 2014/0275852 A1 | 9/2014 | Hong et al. |
| 2014/0276167 A1 | 9/2014 | Dasgupta et al. |
| 2014/0276618 A1 | 9/2014 | Di Caprio |
| 2014/0276920 A1 | 9/2014 | Hendrick et al. |
| 2014/0276923 A1 | 9/2014 | Miller |
| 2014/0288525 A1 | 9/2014 | Fudaba et al. |
| 2014/0296889 A1 | 10/2014 | Avneri et al. |
| 2014/0309533 A1 | 10/2014 | Yamashita et al. |
| 2014/0330286 A1 | 11/2014 | Wallace |
| 2014/0343537 A1 | 11/2014 | Eversull et al. |
| 2014/0350645 A1 | 11/2014 | Diller et al. |
| 2014/0358123 A1 | 12/2014 | Ueda |
| 2014/0371718 A1 | 12/2014 | Alvarez et al. |
| 2015/0005704 A1 | 1/2015 | Heisel et al. |
| 2015/0046148 A1 | 2/2015 | Oh et al. |
| 2015/0105729 A1 | 4/2015 | Valeti et al. |
| 2015/0119859 A1 | 4/2015 | Cajamarca et al. |
| 2015/0126861 A1 | 5/2015 | Gambhir et al. |
| 2015/0133978 A1 | 5/2015 | Paul, Jr. |
| 2015/0157220 A1 | 6/2015 | Fish et al. |
| 2015/0157772 A1 | 6/2015 | Li et al. |
| 2015/0173782 A1 | 6/2015 | Garrison et al. |
| 2015/0174363 A1 | 6/2015 | Sutermeister et al. |
| 2015/0257659 A1 | 9/2015 | Broers et al. |
| 2015/0269825 A1 | 9/2015 | Tran |
| 2015/0290390 A1 | 10/2015 | Ring et al. |
| 2015/0335288 A1 | 11/2015 | Toth et al. |
| 2015/0335857 A1 | 11/2015 | Ishikawa |
| 2015/0359547 A1* | 12/2015 | Vale ........................ A61M 1/84 606/115 |
| 2015/0366518 A1 | 12/2015 | Sampson |
| 2016/0000443 A1 | 1/2016 | Lilburn et al. |
| 2016/0008572 A1 | 1/2016 | Di Caprio |
| 2016/0030079 A1 | 2/2016 | Cohen |
| 2016/0038174 A1 | 2/2016 | Bruzzi et al. |
| 2016/0051386 A1 | 2/2016 | Haarmann-Theimann |
| 2016/0058459 A1 | 3/2016 | Bowman |
| 2016/0081825 A1 | 3/2016 | Sudin et al. |
| 2016/0100819 A1 | 4/2016 | Tieu |
| 2016/0128688 A1 | 5/2016 | Garrison et al. |
| 2016/0129221 A1 | 5/2016 | Haverkost et al. |
| 2016/0135829 A1 | 5/2016 | Holochwost et al. |
| 2016/0144157 A1 | 5/2016 | Gulachenski et al. |
| 2016/0151010 A1 | 6/2016 | Erez |
| 2016/0166265 A1 | 6/2016 | Nita |
| 2016/0166266 A1 | 6/2016 | Nita |
| 2016/0199204 A1 | 7/2016 | Pung et al. |
| 2016/0199620 A1 | 7/2016 | Pokorney |
| 2016/0206216 A1 | 7/2016 | Kirenko |
| 2016/0206322 A1 | 7/2016 | Fitz et al. |
| 2016/0213396 A1 | 7/2016 | Dowell et al. |
| 2016/0220741 A1 | 8/2016 | Garrison et al. |
| 2016/0242764 A1 | 8/2016 | Garrison et al. |
| 2016/0242893 A1 | 8/2016 | Joshi et al. |
| 2016/0243157 A1 | 8/2016 | Cruise et al. |
| 2016/0256611 A1 | 9/2016 | Fitz |
| 2016/0270806 A1 | 9/2016 | Wallace |
| 2016/0271315 A1 | 9/2016 | Chang |
| 2016/0296690 A1 | 10/2016 | Kume et al. |
| 2016/0311990 A1 | 10/2016 | Cruise et al. |
| 2016/0317156 A1 | 11/2016 | Fitz et al. |
| 2016/0317288 A1 | 11/2016 | Rogers et al. |
| 2016/0345904 A1 | 12/2016 | Bowman |
| 2016/0346508 A1 | 12/2016 | Williams et al. |
| 2016/0346515 A1 | 12/2016 | Buller |
| 2016/0354532 A1 | 12/2016 | Olesky et al. |
| 2016/0361180 A1 | 12/2016 | Vong et al. |
| 2016/0361459 A1 | 12/2016 | Baldwin |
| 2016/0367274 A1 | 12/2016 | Wallace |
| 2016/0367275 A1 | 12/2016 | Wallace |
| 2017/0007264 A1 | 1/2017 | Cruise et al. |
| 2017/0007277 A1 | 1/2017 | Drapeau et al. |
| 2017/0020540 A1 | 1/2017 | Chou et al. |
| 2017/0027604 A1 | 2/2017 | Wallace |
| 2017/0028170 A1 | 2/2017 | Ho |
| 2017/0035436 A1 | 2/2017 | Morita |
| 2017/0035446 A1 | 2/2017 | Rapaport et al. |
| 2017/0042548 A1 | 2/2017 | Lam |
| 2017/0043124 A1 | 2/2017 | Vreeman |
| 2017/0056061 A1 | 3/2017 | Ogle et al. |
| 2017/0071624 A1 | 3/2017 | McGuckin et al. |
| 2017/0072163 A1 | 3/2017 | Lim et al. |
| 2017/0072165 A1 | 3/2017 | Lim et al. |
| 2017/0072452 A1 | 3/2017 | Monetti et al. |
| 2017/0079680 A1 | 3/2017 | Bowman |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0087340 A1 | 3/2017 | Peralta et al. |
| 2017/0100126 A1 | 4/2017 | Bowman et al. |
| 2017/0100142 A1* | 4/2017 | Look ...................... A61B 17/22 |
| 2017/0105743 A1 | 4/2017 | Vale et al. |
| 2017/0143938 A1* | 5/2017 | Ogle ................. A61M 25/0074 |
| 2017/0147765 A1 | 5/2017 | Mehta |
| 2017/0164964 A1 | 6/2017 | Galdonik et al. |
| 2017/0172581 A1 | 6/2017 | Bose et al. |
| 2017/0172766 A1 | 6/2017 | Vong et al. |
| 2017/0181835 A1 | 6/2017 | Kleshinski et al. |
| 2017/0189033 A1 | 7/2017 | Sepetka et al. |
| 2017/0209260 A1 | 7/2017 | Garrison et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224953 A1 | 8/2017 | Tran et al. |
| 2017/0238950 A1 | 8/2017 | Yang et al. |
| 2017/0238953 A1 | 8/2017 | Yang et al. |
| 2017/0246014 A1 | 8/2017 | Rapaport et al. |
| 2017/0252057 A1 | 9/2017 | Bonnette et al. |
| 2017/0259037 A1 | 9/2017 | Kern et al. |
| 2017/0265869 A1 | 9/2017 | Cibulski et al. |
| 2017/0265983 A1 | 9/2017 | Lam et al. |
| 2017/0274180 A1 | 9/2017 | Garrison et al. |
| 2017/0281192 A1 | 10/2017 | Tieu et al. |
| 2017/0281204 A1 | 10/2017 | Garrison et al. |
| 2017/0283536 A1 | 10/2017 | Cruise et al. |
| 2017/0303949 A1 | 10/2017 | Jacobi et al. |
| 2017/0340867 A1 | 11/2017 | Accisano |
| 2017/0348514 A1 | 12/2017 | Guyon et al. |
| 2017/0354421 A1 | 12/2017 | Maguire et al. |
| 2017/0354523 A1 | 12/2017 | Chou et al. |
| 2017/0354803 A1 | 12/2017 | Kume et al. |
| 2017/0360450 A1 | 12/2017 | Tompkins et al. |
| 2017/0361072 A1 | 12/2017 | Chou |
| 2017/0367713 A1 | 12/2017 | Green et al. |
| 2017/0367857 A1 | 12/2017 | Bennett et al. |
| 2017/0368296 A1 | 12/2017 | Chang |
| 2017/0368309 A1 | 12/2017 | Garrison et al. |
| 2018/0008294 A1 | 1/2018 | Garrison et al. |
| 2018/0008439 A9 | 1/2018 | Tieu et al. |
| 2018/0014840 A1 | 1/2018 | Paniam |
| 2018/0028205 A1 | 2/2018 | Chou et al. |
| 2018/0028209 A1 | 2/2018 | Sudin et al. |
| 2018/0036155 A1 | 2/2018 | Tieu et al. |
| 2018/0042623 A1 | 2/2018 | Batiste |
| 2018/0055364 A1 | 3/2018 | Pierro |
| 2018/0055516 A1 | 3/2018 | Bagaoisan et al. |
| 2018/0104390 A1 | 4/2018 | Kilcran |

(56) References Cited

U.S. PATENT DOCUMENTS

| | | |
|---|---|---|
| 2018/0193026 A1 | 7/2018 | Yang |
| 2018/0200478 A1 | 7/2018 | Lorenzo et al. |
| 2018/0207395 A1 | 7/2018 | Bulman et al. |
| 2018/0207399 A1 | 7/2018 | Chou et al. |
| 2018/0228502 A1 | 8/2018 | Shaffer |
| 2018/0242962 A1 | 8/2018 | Walen et al. |
| 2018/0242980 A1 | 8/2018 | Lubock |
| 2018/0242989 A1 | 8/2018 | Nita |
| 2018/0242999 A1 | 8/2018 | Thatipelli |
| 2018/0250013 A1 | 9/2018 | Wallace et al. |
| 2018/0263632 A1 | 9/2018 | Seifert et al. |
| 2018/0263642 A1 | 9/2018 | Nita |
| 2018/0279965 A1 | 10/2018 | Pandit et al. |
| 2018/0289340 A1 | 10/2018 | Trindade Rodrigues et al. |
| 2018/0296236 A1 | 10/2018 | Goldfarb et al. |
| 2018/0353194 A1 | 12/2018 | Shaffer et al. |
| 2019/0022363 A1 | 1/2019 | Grayzel et al. |
| 2019/0029825 A1 | 1/2019 | Fitterer et al. |
| 2019/0070387 A1 | 3/2019 | Goyal |
| 2019/0108540 A1 | 4/2019 | Look et al. |
| 2019/0167124 A1 | 6/2019 | Verkruijsse et al. |
| 2019/0175030 A1 | 6/2019 | Verkruijsse et al. |
| 2019/0200871 A1 | 7/2019 | De Haan |
| 2019/0239910 A1 | 8/2019 | Brade et al. |
| 2019/0275290 A1 | 9/2019 | Yamashita et al. |
| 2019/0290884 A1 | 9/2019 | Kanemasa et al. |
| 2019/0329003 A1 | 10/2019 | Watanabe |
| 2019/0336142 A1 | 11/2019 | Torrie |
| 2019/0336149 A1 | 11/2019 | Yang |
| 2019/0336727 A1 | 11/2019 | Yang |
| 2019/0351182 A1 | 11/2019 | Chou et al. |
| 2019/0366041 A1 | 12/2019 | Yang |
| 2020/0001046 A1 | 1/2020 | Yang |
| 2020/0009301 A1 | 1/2020 | Yee |
| 2020/0009350 A1 | 1/2020 | Goyal |
| 2020/0022712 A1 | 1/2020 | Deville et al. |
| 2020/0023160 A1 | 1/2020 | Chou et al. |
| 2020/0046368 A1 | 2/2020 | Merritt et al. |
| 2020/0046937 A1 | 2/2020 | Nakagawa et al. |
| 2020/0170521 A1 | 6/2020 | Gupta et al. |
| 2020/0171276 A1 | 6/2020 | Onozuka |
| 2020/0171277 A1 | 6/2020 | Garrison et al. |
| 2020/0188630 A1 | 6/2020 | Fujita et al. |
| 2020/0025845 A1 | 7/2020 | Yang et al. |
| 2020/0205845 A1 | 7/2020 | Yang et al. |
| 2020/0276411 A1 | 9/2020 | Ogle et al. |
| 2020/0289136 A1 | 9/2020 | Chou |
| 2020/0297362 A1 | 9/2020 | Devill et al. |
| 2020/0297972 A1 | 9/2020 | Yee |
| 2020/0306501 A1 | 10/2020 | Yee |
| 2020/0323535 A1 | 10/2020 | Yang |
| 2020/0337716 A1 | 10/2020 | Garrison et al. |
| 2020/0345979 A1 | 11/2020 | Loh et al. |
| 2021/0001141 A1 | 1/2021 | Pfiffner et al. |
| 2021/0045758 A1 | 2/2021 | Garrison et al. |
| 2021/0052296 A1 | 2/2021 | Garrison |
| 2021/0068852 A1 | 3/2021 | Spence |
| 2021/0093336 A1 | 4/2021 | Roue |
| 2021/0106238 A1 | 4/2021 | Strasser |
| 2021/0106792 A1 | 4/2021 | Rafiee |
| 2021/0128182 A1 | 5/2021 | Teigen et al. |
| 2021/0146094 A1 | 5/2021 | Christian et al. |
| 2021/0153744 A1 | 5/2021 | Pierro |
| 2021/0186537 A1 | 6/2021 | Buck et al. |
| 2021/0186542 A1 | 6/2021 | Buck et al. |
| 2021/0187244 A1 | 6/2021 | Buck et al. |
| 2021/0315596 A1 | 10/2021 | Buck et al. |
| 2021/0315597 A1 | 10/2021 | Buck et al. |
| 2021/0315598 A1 | 10/2021 | Buck et al. |
| 2021/0316121 A1 | 10/2021 | Buck et al. |
| 2021/0316127 A1 | 10/2021 | Buck et al. |
| 2021/0361366 A1 | 11/2021 | Murphy et al. |
| 2021/0361909 A1 | 11/2021 | Cottone et al. |
| 2021/0378527 A1 | 12/2021 | Strasser et al. |
| 2021/0378696 A1 | 12/2021 | Yang et al. |
| 2022/0047849 A1 | 2/2022 | Yee et al. |
| 2022/0211975 A1 | 7/2022 | Yang et al. |

FOREIGN PATENT DOCUMENTS

| | | |
|---|---|---|
| DE | 10 2010 053111 | 6/2012 |
| DE | 10 2012 112732 | 6/2014 |
| EP | 0 330 843 | 12/1993 |
| EP | 0 582 533 | 2/1994 |
| EP | 0 309 471 | 8/1996 |
| EP | 1 349 486 | 3/2008 |
| EP | 2 069 528 | 3/2013 |
| EP | 2 937 108 | 10/2015 |
| EP | 2 928 360 | 1/2017 |
| EP | 2 211 732 | 5/2018 |
| EP | 3 539 486 | 9/2019 |
| EP | 3 698 740 | 8/2020 |
| GB | 2077132 | 12/1981 |
| JP | 2002-535049 | 10/2002 |
| JP | 2003-527925 | 9/2003 |
| JP | 2006-102222 | 4/2006 |
| JP | 2006-521881 | 9/2006 |
| JP | 2008-502378 | 1/2008 |
| JP | 2013-504388 | 2/2013 |
| JP | 2014-515670 | 7/2014 |
| JP | 2015-504327 | 2/2015 |
| WO | WO 1995/009659 | 4/1995 |
| WO | WO 2000/000100 | 1/2000 |
| WO | WO 2009/054968 | 4/2009 |
| WO | WO 2009/132218 | 10/2009 |
| WO | WO 2010/126786 | 11/2010 |
| WO | WO 2014/151209 | 9/2014 |
| WO | WO 2014/203336 | 12/2014 |
| WO | WO 2017/025775 | 2/2017 |
| WO | WO 2018/121363 | 7/2018 |
| WO | WO 2019/178165 | 9/2019 |
| WO | WO 2019/222518 | 11/2019 |
| WO | WO 2019/246583 | 12/2019 |
| WO | WO 2020/145928 | 7/2020 |
| WO | WO 2021/016213 | 1/2021 |
| WO | WO 2021/064955 | 4/2021 |
| WO | WO 2021/090821 | 5/2021 |
| WO | WO 2021/105658 | 6/2021 |
| WO | WO 2021/242734 | 12/2021 |

OTHER PUBLICATIONS

International Search Report and Written Opinion dated Sep. 30, 2019 in Application No. PCT/US19/040691.

Merit Medical Systems Acquired Distal Access's SPINR Platform, Jul. 15, 2015, Digital Access, LLC; Merit Medical Systems, 5 pages.

Simon et al., *Exploring the efficacy of cyclic vs. static aspiration in a cerebral thrombectomy model: an initial proof of concept study*, J. NeuroInvent Surg 2014, 6 pp. 677-683.

Simon et al., *Hydrodynamic comparison of the Penumbra system and commonly available syringes in forced-suction thrombectomy*, J. NeuroInvent Surg 2014, 6, pp. 205-211.

Spiotta et al., Evolution of thrombectomy approaches and devices for acute stroke: a technical review, J. Neuro Intervent Surg 2015, 7, pp. 2-7.

Abay et al., 2014, Investigation of photoplethysmography and Near Infrared Spectroscopy for the assessment of tissue blood perfusion, 36th Annual International Conference of the IEEE Engineering in Medicine and Biology Society, Chicago, IL, pp. 5361-5364, doi: 10.1109/EMBC.2014.6944837.

Korpelainen et al., 1995, Asymmetrical skin temperature in ischemic stroke, Stroke, 26(9):1543-1547.

Bernava et al., Sep. 23, 2019, Direct trhomboaspiration efficacy for mechanical thrombectomy is related to the angle of interaction between the catheter and the clot, J. NeuroIntervent Surg., 0:1-6, doi:10.1136/neurintsurg-2019-015113.

\* cited by examiner

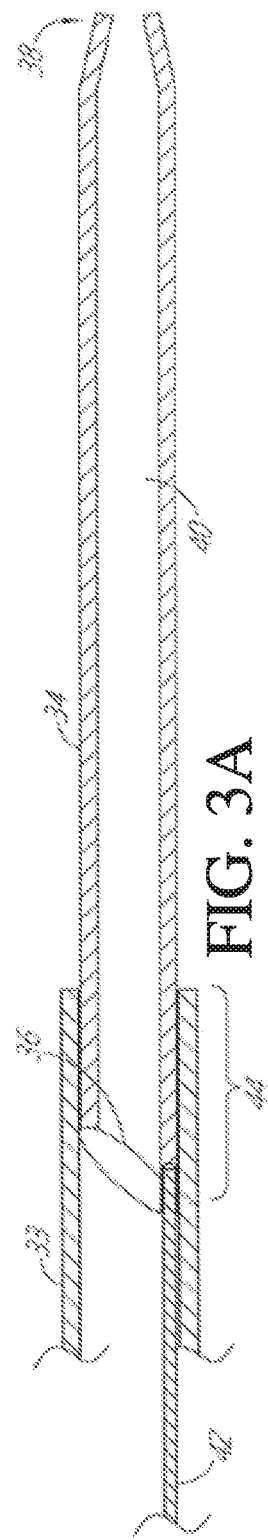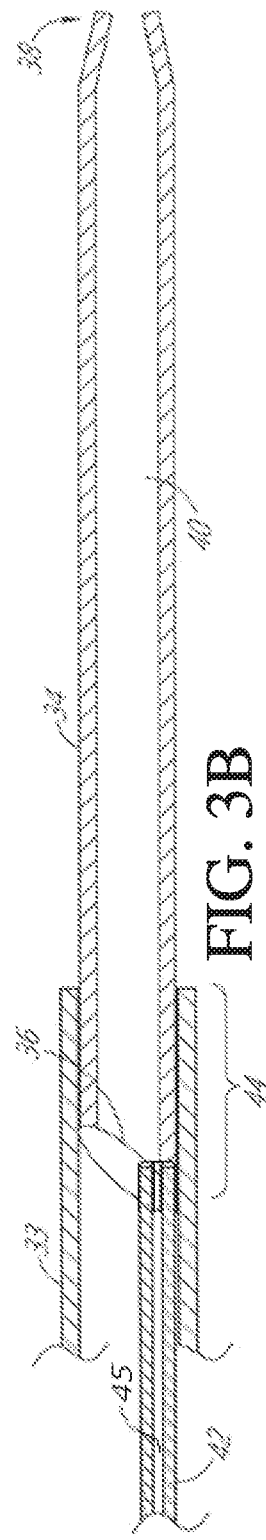

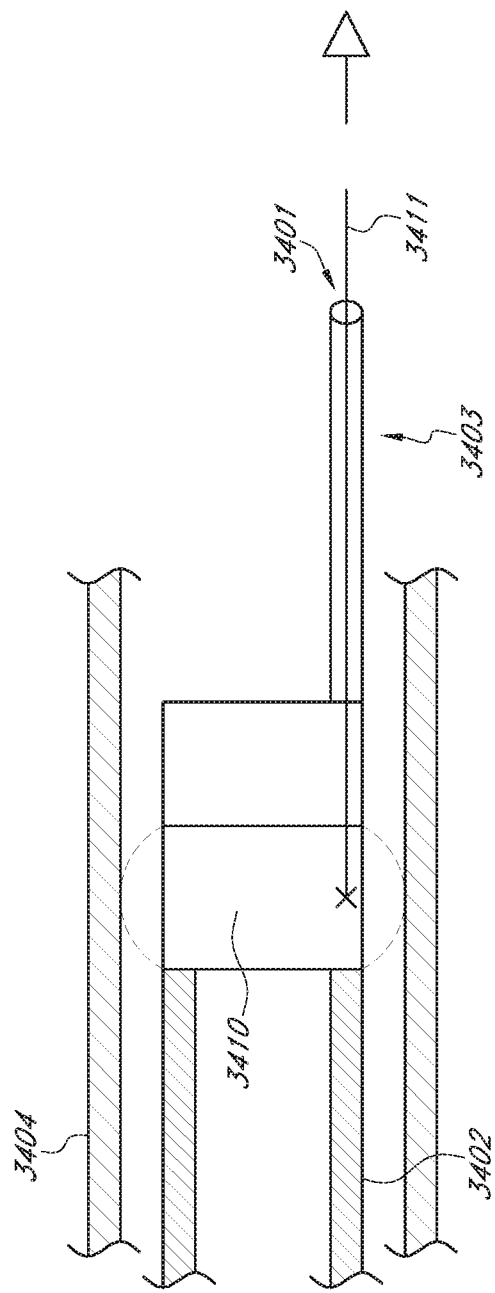

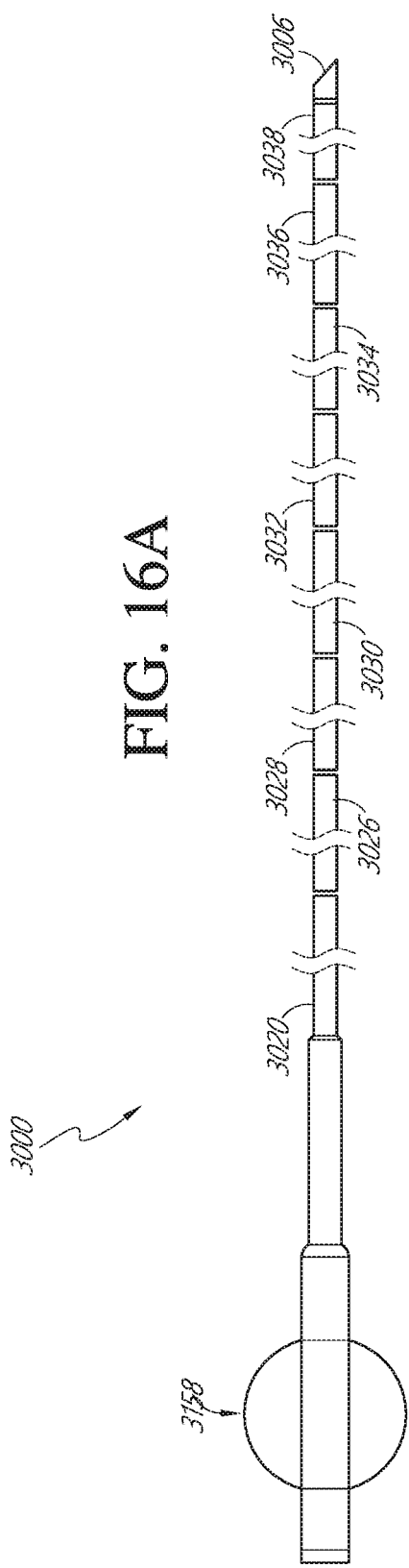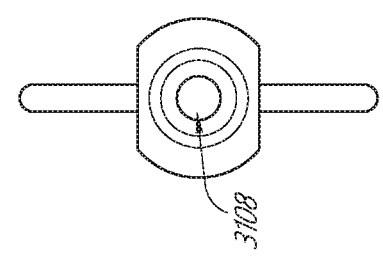

SEALED NEUROVASCULAR EXTENDABLE CATHETER

CROSS-REFERENCE TO RELATED APPLICATIONS

This application claims the benefit of U.S. Provisional Application No. 62/694,796, filed Jul. 6, 2018, the entirety of this application is hereby incorporated by reference herein.

BACKGROUND

Stroke is the third most common cause of death in the United States and the most disabling neurologic disorder. Approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. Its incidence increases with age. Risk factors for stroke include systolic or diastolic hypertension, hypercholesterolemia, cigarette smoking, heavy alcohol consumption, and oral contraceptive use.

Hemorrhagic stroke accounts for 20% of the annual stroke population. Hemorrhagic stroke often occurs due to rupture of an aneurysm or arteriovenous malformation bleeding into the brain tissue, resulting in cerebral infarction. The remaining 80% of the stroke population are ischemic strokes and are caused by occluded vessels that deprive the brain of oxygen-carrying blood. Ischemic strokes are often caused by emboli or pieces of thrombotic tissue that have dislodged from other body sites or from the cerebral vessels themselves to occlude in the narrow cerebral arteries more distally. When a patient presents with neurological symptoms and signs which resolve completely within 1 hour, the term transient ischemic attack (TIA) is used. Etiologically, TIA and stroke share the same pathophysiologic mechanisms and thus represent a continuum based on persistence of symptoms and extent of ischemic insult.

Emboli occasionally form around the valves of the heart or in the left atrial appendage during periods of irregular heart rhythm and then are dislodged and follow the blood flow into the distal regions of the body. Those emboli can pass to the brain and cause an embolic stroke. As will be discussed below, many such occlusions occur in the middle cerebral artery (MCA), although such is not the only site where emboli come to rest.

When a patient presents with neurological deficit, a diagnostic hypothesis for the cause of stroke can be generated based on the patient's history, a review of stroke risk factors, and a neurologic examination. If an ischemic event is suspected, a clinician can tentatively assess whether the patient has a cardiogenic source of emboli, large artery extracranial or intracranial disease, small artery intraparenchymal disease, or a hematologic or other systemic disorder. A head CT scan is often performed to determine whether the patient has suffered an ischemic or hemorrhagic insult. Blood would be present on the CT scan in subarachnoid hemorrhage, intraparenchymal hematoma, or intraventricular hemorrhage.

Traditionally, emergent management of acute ischemic stroke consisted mainly of general supportive care, e.g. hydration, monitoring neurological status, blood pressure control, and/or anti-platelet or anti-coagulation therapy. In 1996, the Food and Drug Administration approved the use of Genentech Inc.'s thrombolytic drug, tissue plasminogen activator (t-PA) or Activase®, for treating acute stroke. A randomized, double-blind trial, the National Institute of Neurological Disorders and t-PA Stroke Study, revealed a statistically significant improvement in stoke scale scores at 24 hours in the group of patients receiving intravenous t-PA within 3 hours of the onset of an ischemic stroke. Since the approval of t-PA, an emergency room physician could, for the first time, offer a stroke patient an effective treatment besides supportive care.

However, treatment with systemic t-PA is associated with increased risk of intracerebral hemorrhage and other hemorrhagic complications. Patients treated with t-PA were more likely to sustain a symptomatic intracerebral hemorrhage during the first 36 hours of treatment. The frequency of symptomatic hemorrhage increases when t-PA is administered beyond 3 hours from the onset of a stroke. Besides the time constraint in using t-PA in acute ischemic stroke, other contraindications include the following: if the patient has had a previous stroke or serious head trauma in the preceding 3 months, if the patient has a systolic blood pressure above 185 mm Hg or diastolic blood pressure above 110 mmHg, if the patient requires aggressive treatment to reduce the blood pressure to the specified limits, if the patient is taking anticoagulants or has a propensity to hemorrhage, and/or if the patient has had a recent invasive surgical procedure. Therefore, only a small percentage of selected stroke patients are qualified to receive t-PA.

Obstructive emboli have also been mechanically removed from various sites in the vasculature for years. Mechanical therapies have involved capturing and removing the clot, dissolving the clot, disrupting and suctioning the clot, and/or creating a flow channel through the clot. One of the first mechanical devices developed for stroke treatment is the MERCI Retriever System (Concentric Medical, Redwood City, Calif.). A balloon-tipped guide catheter is used to access the internal carotid artery (ICA) from the femoral artery. A microcatheter is placed through the guide catheter and used to deliver the coil-tipped retriever across the clot and is then pulled back to deploy the retriever around the clot. The microcatheter and retriever are then pulled back, with the goal of pulling the clot, into the balloon guide catheter while the balloon is inflated and a syringe is connected to the balloon guide catheter to aspirate the guide catheter during clot retrieval. This device has had initially positive results as compared to thrombolytic therapy alone.

Other thrombectomy devices utilize expandable cages, baskets, or snares to capture and retrieve clot. Temporary stents, sometimes referred to as stentrievers or revascularization devices, are utilized to remove or retrieve clot as well as restore flow to the vessel. A series of devices using active laser or ultrasound energy to break up the clot have also been utilized. Other active energy devices have been used in conjunction with intra-arterial thrombolytic infusion to accelerate the dissolution of the thrombus. Many of these devices are used in conjunction with aspiration to aid in the removal of the clot and reduce the risk of emboli. Suctioning of the clot has also been used with single-lumen catheters and syringes or aspiration pumps, with or without adjunct disruption of the clot. Devices which apply powered fluid vortices in combination with suction have been utilized to improve the efficacy of this method of thrombectomy. Finally, balloons or stents have been used to create a patent lumen through the clot when clot removal or dissolution was not possible.

Notwithstanding the foregoing, there remains a need for new devices and methods for treating vasculature occlusions in the body, including acute ischemic stroke and occlusive cerebrovascular disease.

SUMMARY

Disclosed herein is a sealed neurovascular extendable catheter having an outer catheter, an inner catheter, and an annular gap between an outer surface of the inner catheter and an inner surface of the outer catheter. The outer catheter has a proximal end and a distal end and the inner catheter has a proximal end and a distal end. The outer catheter is extendable through the outer catheter such that the distal end of the inner catheter is configured to extend beyond the distal end of the outer catheter. The extendable catheter also has a sealing feature positioned between the inner catheter and the outer catheter. The sealing feature is configured to fluidly seal at least a portion of a length of the annular gap. The sealing feature is configured to allow axial translation of the inner catheter relative to the outer catheter.

The sealing feature may have at least one annular protrusion extending around a circumference of the inner catheter. The at least one protrusion may be compliant and may comprise an outer diameter slightly larger than an inner diameter of the outer catheter. The at least one protrusion may be a plurality of protrusions. The at least one protrusion may have a chevron-shape pointing in the distal direction and/or a chevron-shape pointing in the proximal direction. The protrusion may be a skirt-shaped protrusion configured to allow distal fluid flow but not proximal fluid flow through the sealing feature.

The sealing feature may be an expandable bulge surrounding a circumference of the inner catheter. The expandable bulge may have a sealed configuration in which an outer diameter of the expandable bulge seals the annular gap and an unsealed configuration in which the outer diameter of the expandable bulge does not seal the annular gap. The expandable bulge may be mechanically expandable. The expandable bulge may be positioned at a proximal end of the inner catheter. A tension cable may be joined to the expandable bulge at or near a distal end of the expandable bulge and pulling the tension cable proximally may be configured to axially contract and radially expand the expandable bulge. The expandable bulge may be expandable in response to receiving an electric current and/or in response to stimulation by light. The expandable bulge may be a hydrogel. The expandable bulge may be inflatable. The inner catheter may have a proximal spine having a lumen. The lumen may be configured to transmit a stimulus to the expandable bulge for activating the expandable bulge and causing it to expand.

The sealing feature may be an elastic flange positioned at a distal tip of the outer catheter. The elastic flange may have an inner diameter smaller than an outer diameter of the inner catheter.

The sealing feature may be a hub having an expanded diameter. The hub may be positioned at a proximal end of the inner catheter and be configured to form an interference fit with an inner diameter of the outer catheter. The inner catheter may have a proximal spine having a lumen. The lumen may extend through the hub to form a fluid port through the sealing feature. A flushing solution may be delivered through the fluid port to the annular gap in a space distal to the sealing feature.

The sealing feature may have a proximal sliding ring and a distal sliding ring surrounding the inner catheter. Each sliding ring may have an inner annulus configured to form a sliding interference fit around the inner catheter and an outer annulus configured to form a sliding interference fit with an inner diameter of the outer catheter. Each sliding ring may have a plurality of spokes joining the inner annulus and the outer annulus. The sealing feature may have one or more springs surrounding the inner catheter and joining the inner annulus of the proximal sliding ring to the inner annulus of the distal sliding ring and an elastic membrane configured to form a fluid barrier. The elastic membrane may be coupled to the one or more springs such that the fluid barrier circumferentially surrounds the inner catheter and extends from the proximal sliding ring to the distal sliding ring. The sealing feature may further have a ridge feature fixed to an outer surface of the inner catheter. The ridge feature may be positioned between the proximal sliding ring and the distal sliding ring and may be configured to catch and pull the proximal sliding ring in a proximal direction and to catch and pull the distal sliding ring in a distal direction. The one or more springs may force the elastic membrane into compression against an inner surface of the outer catheter to seal the annular gap in an unbiased configuration. Translating the inner catheter to pull one of the sliding rings in a proximal or distal direction may cause the pulled sliding ring to axially extend and radially compress the one or more springs. Radially compressing the one or more springs may cause the elastic membrane to be at least partially retracted from the inner surface of the outer catheter, breaking the fluid seal for a period while the inner catheter is in motion.

The sealing feature may have a large diameter ring surrounding the inner catheter and a small diameter ring surrounding the inner catheter. The large diameter ring may have an inner annulus configured to receive the inner catheter, an outer annulus configured to form a sliding interference fit with an inner diameter of the outer catheter, and a plurality of spokes joining the inner annulus and the outer annulus. The small diameter ring may be positioned either proximally or distally of the large diameter ring and may form a sliding interference fit with an outer surface of the inner catheter. The small diameter ring may have one or more recesses configured to receive one or more key features extending axially along at least a portion of the inner catheter. The one or more recesses may be configured to rotate the small diameter ring with the inner catheter. The sealing feature may also have a torsion spring surrounding the inner catheter and joining the small diameter ring to the large diameter ring and an elastic membrane coupled to the torsion spring. The elastic membrane may be configured to form a fluid barrier circumferentially surrounding the inner catheter and extending from the large diameter ring to the small diameter ring. The torsion spring may force the elastic membrane into compression against an inner surface of the outer catheter to seal the annular gap in an unbiased configuration. Rotating the inner catheter to rotate the small diameter ring may cause the torsion spring to axially extend and radially compress such that elastic membrane is at least partially retracted from the inner surface of the outer catheter, breaking the fluid seal for a period while the inner catheter is in motion.

In another aspect of the present disclosure, disclosed herein is a neurovascular catheter for sealing a blood vessel. The neurovascular catheter has an elongate body having a proximal end and a distal end and a sealing feature configured to fluidly seal an annular gap positioned between an outer surface of the elongate body and the blood vessel. The sealing feature has a compliant annular ring configured to be placed into compression with a wall of the blood vessel without damaging the blood vessel.

The ring may comprise an elastomeric polymer. The ring may be a hydrogel. The hydrogel may be electrosensitive and configured to expand upon receiving an electric current and/or may be photosensitive and configured to expand upon receiving a light stimulus. The hydrogel may be configured to expand upon exposure the intravascular physiological environment. The ring may be inflatable. The outer surface of the elongate body may have a recess for receiving the ring. The ring may be detachable from the elongate body. The ring may be custom-formed to the size of the blood vessel. The neurovascular catheter may further include a replacement ring that is sized differently from the ring and interchangeable with the ring.

Any feature, structure, or step disclosed herein can be replaced with or combined with any other feature, structure, or step disclosed herein, or omitted. Further, for purposes of summarizing the disclosure, certain aspects, advantages, and features of the embodiments have been described herein. It is to be understood that not necessarily any or all such advantages are achieved in accordance with any particular embodiment disclosed herein. No individual aspects of this disclosure are essential or indispensable. Further features and advantages of the embodiments will become apparent to those of skill in the art in view of the Detailed Description which follows when considered together with the attached drawings and claims.

BRIEF DESCRIPTION OF THE DRAWINGS

FIGS. 3A-3B are cross-sectional elevational views of a distal end of catheter 10, with the distal section 34 fully extended.

FIG. 8A depicts an inner catheter comprising a substantially constant diameter. FIG. 8B depicts an inner catheter comprising a reduced distal diameter. FIGS. 8C-8E illustrate close-up side views of an example of chevron-shaped protrusions on the inner device. The view in FIG. 8D is approximately 90 degrees offset around the circumference of the inner device from the view in FIG. 8C. FIG. 8E is the same as FIG. 8C but also showing the orientation of the seal on the back side of the catheter.

FIG. 9 schematically illustrates a device comprising a mechanically expandable bulge for sealing the annular gap.

FIG. 12A depicts the device in a sealed configuration. FIG. 12B depicts the device in an unsealed configuration. FIG. 12C depicts a sliding ring used in the spring sealing feature.

FIG. 13A depicts the device in an unsealed configuration.

FIG. 13B depicts a cross section of the inner catheter including a plurality of key features for rotating the torsion spring. FIG. 13C depicts a ring actuated by the key features to turn the torsion spring.

FIG. 16A illustrates a side elevational view of a progressively enhanced flexibility catheter according to an embodiment.

FIG. 16B is a proximal end view of the enhanced flexibility catheter of FIG. 34A.

DETAILED DESCRIPTION

Figure 1:
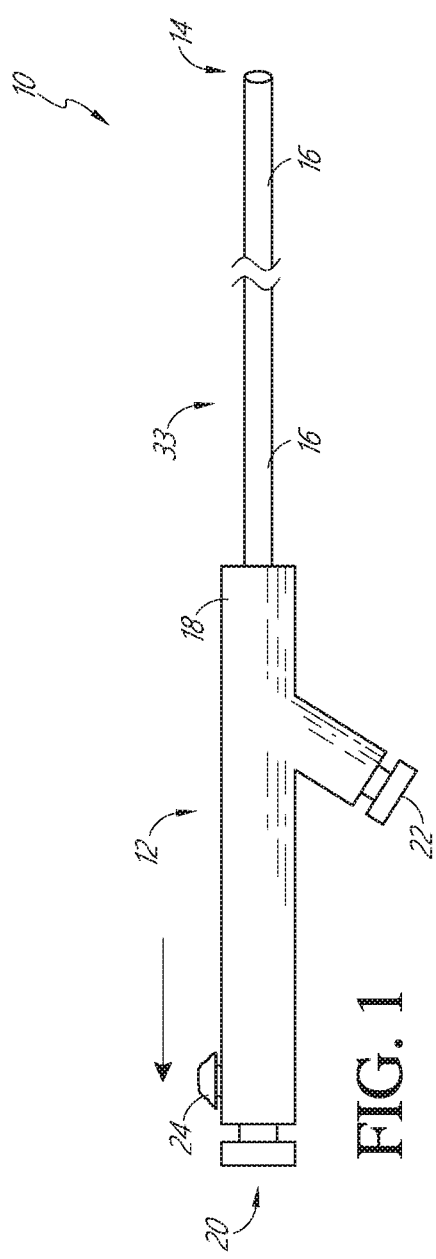
FIG. 1 is a side elevational schematic view of an intracranial aspiration catheter in accordance with the present invention, with a distal segment in a proximally retracted configuration.

Referring to FIG. 1, there is disclosed a catheter 10 in accordance with one aspect of the present invention. Although primarily described in the context of an axially extendable distal segment aspiration catheter with a single central lumen, catheters of the present invention can readily be modified to incorporate additional structures, such as permanent or removable column strength enhancing mandrels, two or more lumen such as to permit drug, contrast or irrigant infusion or to supply inflation media to an inflatable balloon carried by the catheter, or combinations of these features, as will be readily apparent to one of skill in the art in view of the disclosure herein. In addition, the present invention will be described primarily in the context of removing obstructive material from remote vasculature in the brain, but has applicability as an access catheter for delivery and removal of any of a variety of diagnostics or therapeutic devices with or without aspiration.

The catheters disclosed herein may readily be adapted for use throughout the body wherever it may be desirable to distally advance a low profile distal catheter segment from a larger diameter proximal segment. For example, axially extendable catheter shafts in accordance with the present invention may be dimensioned for use throughout the coronary and peripheral vasculature, the gastrointestinal tract, the urethra, ureters, Fallopian tubes and other lumens and potential lumens, as well. The telescoping structure of the present invention may also be used to provide minimally invasive percutaneous tissue access, such as for diagnostic or therapeutic access to a solid tissue target (e.g., breast or liver or brain biopsy or tissue excision), delivery of laparoscopic tools or access to bones such as the spine for delivery of screws, bone cement or other tools or implants.

The catheter 10 generally comprises an elongate tubular body 16 extending between a proximal end 12 and a distal functional end 14. The length of the tubular body 16 depends upon the desired application. For example, lengths in the area of from about 120 cm to about 140 cm or more are typical for use in femoral access percutaneous transluminal coronary applications. Intracranial or other applications may call for a different catheter shaft length depending upon the vascular access site, as will be understood in the art.

Figure 2:
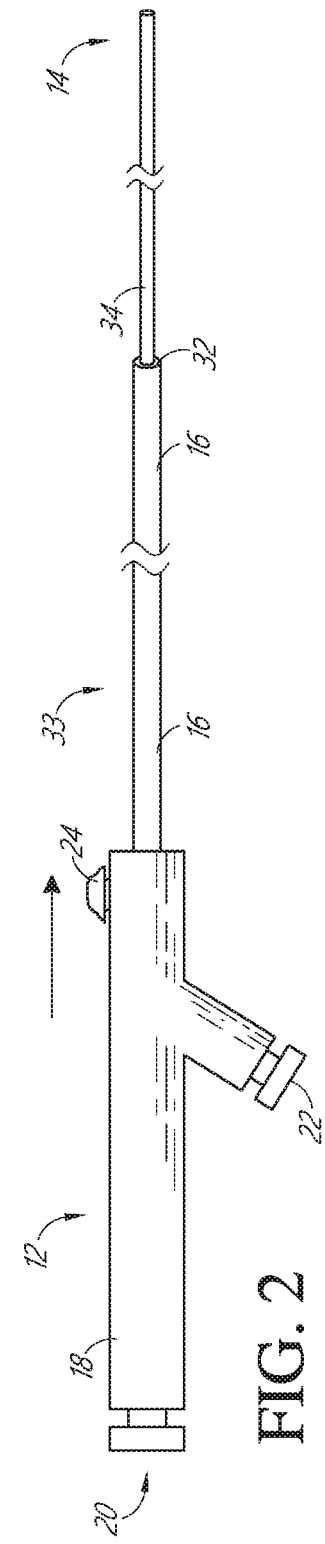
FIG. 2 is a side elevational view as in FIG. 1, with the distal segment in a distally extended configuration.

In the illustrated embodiment, the tubular body 16 is divided into at least a fixed proximal section 33 and an axially extendable and retractable distal section 34 separated at a transition 32. FIG. 2 is a side elevational view of the catheter 10 shown in FIG. 1, with the distal segment in a distally extended configuration.

Referring to FIGS. 3A and 3B, there is illustrated a cross-sectional view of the distal segment 34 shown extended distally from the proximal segment 33 in accordance with the present invention. Distal segment 34 extends between a proximal end 36 and a distal end 38 and defines at least one elongate central lumen 40 extending axially therethrough. Distal end 38 may be provided with one or more movable side walls or jaws 39, which move laterally in the direction of an opposing side wall or jaw 41 under the influence of aspiration, to enable the distal end 38 to bite or break thrombus or other material into smaller particles, to facilitate aspiration through lumen 40. Both walls 39 and 41 may be movable towards and away from each other to break up thrombus as is discussed further below.

The inner diameter of the distal section 34 may be between about 0.030 inches and about 0.112 inches, between about 0.040 inches and about 0.102 inches, between about 0.045 inches and about 0.097 inches, between about 0.050 inches and about 0.092 inches, between about 0.055 inches and about 0.087 inches, between about 0.060 inches and about 0.082 inches, between about 0.062 inches and about 0.080 inches, between about 0.064 inches and about 0.078 inches, between about 0.066 inches and about 0.076 inches, between about 0.068 inches and about 0.074 inches, or between about 0.070 inches and about 0.072 inches.

The inner diameter and the outer diameter of the distal section 34 may be constant or substantially constant along its longitudinal length. The inner diameter may be at least about 0.06 inches, 0.065 inches, 0.07 inches, 0.075 inches, 0.08 inches, or more than 0.08 inches. The outer diameter may be at least about 0.07 inches, 0.075 inches, 0.08 inches, 0.085 inches, 0.09 inches, 0.095 inches, 0.1 inches, or more than 0.1 inches. The total thickness of the sidewall extending between the inner and outer diameter may be at least about 0.005 inches, 0.010 inches, 0.015 inches, 0.02 inches, 0.025 inches, or more than 0.025 inches. For example, the distal section may 34 may have an inner diameter of about 0.071 inches and an outer diameter of about 0.083 inches. Alternatively, the distal section 34 may be tapered near its distal end. A larger lumen (internal diameter) may increase the applied aspiration force through the distal end of the distal section 34. A smaller outer diameter may provide better catheter trackability and/or may better enable the catheter to reach more distal anatomy (e.g. neuroanatomy), as the tapered distal end may be better accommodated in smaller blood vessels. The inner and outer diameters of the distal section 34 may be correlated in order to maintain a sufficient sidewall thickness that provides sufficient structural integrity to the catheter. The distal section 34 may be tapered at less than or equal to about 5 cm, about 10 cm, about 15 cm, about 20 cm, about 23 cm, about 25 cm, about 30 cm, about 31 cm, about 35 cm, about 40 cm, about 45 cm, about 50 cm, about 60 cm, or about 70 cm from its distal end. In some embodiments, the taper may be positioned between about 25 cm and about 35 cm from the distal end of the distal section 34. In some embodiments, the taper may be positioned between about 15 cm and about 25 cm from the distal end of the distal section 34.

The inner diameter of the distal section 34 may be tapered or decreased in the distal direction near the distal end to an internal diameter that is less than or equal to about 95%, about 90%, about 85%, about 80%, about 75%, about 70%, about 65%, about 60%, about 55%, or about 50% of the adjacent, untapered internal diameter. In some embodiments, the internal diameter of the tapered distal section 34 may be between about 50% and about 70% of the adjacent, untapered internal diameter. For example, the untapered internal diameter at the proximal end of the distal section 34 may be about 0.071 inches and the tapered internal diameter at the distal end of the distal section 34 may be about 0.035 inches, 0.045 inches, or 0.055 inches. The inner diameter of the distal section 34 may be tapered or increased near the distal end by greater than or equal to about 102%, 104%, 106%, 108%, or more of the internal diameter just proximal to a transition into the taper. The tapered inner diameter of the distal section 34 may be less than or equal to about 0.11 inches, about 0.1 inches, about 0.090 inches, about 0.080 inches, about 0.070 inches, about 0.065 inches, about 0.060 inches, about 0.055 inches, about 0.050 inches, about 0.045 inches, about 0.040 inches, about 0.035 inches, about 0.030 inches, about 0.025 inches, about 0.020 inches, about 0.015 inches, or about 0.010 inches. The taper in the outer diameter of the tapered portion of the distal section 34 may be matched to maintain a constant thickness of the sidewall. Alternatively, the sidewall may be thinner along the tapered portion. For instance, the sidewall may be no greater than 95%, 90%, 85%, 80%, 75%, 70%, or less than 70% of the thickness of the sidewall along the proximal portion of the distal section 34. In some embodiments, the length of the distal tapered portion of the distal section 34 may be between about 25 cm and about 35 cm, between about 25 cm and about 30 cm, between about 30 cm and 35 cm, or approximately 30 cm.

In some embodiments, the proximal segment 33 may have an inner diameter of at least about 0.07 inches, 0.075 inches, 0.08 inches, 0.085 inches, 0.09 inches, 0.1 inches, 0.105 inches, or more than 0.105 inches. The proximal segment 33 may have an outer diameter of at least about 0.08 inches, 0.085 inches, 0.09 inches, 0.095 inches, 0.01 inches, 0.105 inches, 0.11 inches, 0.0115 inches, 0.012 inches, or more than 0.012 inches. For example, the inner diameter may be approximately 0.088 inches and the outer diameter may be approximately 0.106 inches. The sidewall of the proximal segment 33 may have a thickness of at least about 0.005 inches, 0.01 inches, 0.015 inches, 0.02 inches, 0.025 inches, or more than 0.25 inches. In some embodiments, the proximal segment 33 has a constant inner and/or outer diameter along its length. In some embodiments, the proximal segment 33 may slightly taper or decrease in diameter along the distal direction. For example, in some embodiments, the outer diameter of the proximal segment 33 may be about 0.106 inches at the distal end and about 0.108 inches at the proximal end.

The length of the proximal segment 33 may be at least about 90 cm, 95 cm, 100 cm, 105 cm, 110 cm, 115 cm, 120 cm, 125 cm, 130 cm, 135 cm, or more than 135 cm. For example, in one embodiment the length is approximately 106 cm. In another embodiment, the length is approximately 117 cm. In some neurovascular applications, the distal end of the proximal segment 33 may extend at least to the Horizontal Petrous segment of the vasculature.

In some embodiments, the length of the distal section 34 may be between about 13 cm and about 53 cm, between about 18 cm and about 48 cm, between about 23 cm and about 43 cm, between about 28 cm and about 38 cm, between about 20 cm and 30 cm, or between about 25 cm and 30 cm. The length of the distal section 34 may be less than or equal to about 20 cm, about 25 cm, about 30 cm, about 33 cm, about 35 cm, about 40 cm, about 41 cm, about 45 cm, about 50 cm, about 55 cm, about 60 cm, about 70 cm, or about 80 cm. The length of the distal section 34 may depend on the degree of tapering of the internal diameter of the distal section 34.

The proximal end 36 of distal section 34 is provided with a proximally extending pull wire 42. Pull wire 42 extends proximally throughout the length of the tubular body 16, to control 24 which may be carried by manifold 18. Axial movement of control 24 produces a corresponding axial movement of distal section 34 with respect to proximal section 33 as has been discussed. Alternatively, the proximal end of pull wire 42 may exit through a port on manifold 18, such that it may be manually grasped and pulled or pushed by the clinician to extend or retract the distal section 34. The length of the pull wire 42 may be between about 700 mm and about 1556 mm, between about 800 mm and about 1456 mm, between about 850 mm and about 1406 mm, between about 900 mm and about 1356 mm, between about 950 mm and about 1306 mm, between about 1000 mm and about 1256 mm, between about 1020 mm and about 1236 mm, between about 1040 mm and about 1216 mm, between about 1060 mm and about 1196 mm, between about 1080 mm and about 1176 mm, between about 1100 mm and about 1156 mm, between about 1110 mm and about 1146 mm, or between about 1120 mm and about 1136 mm. In some preferred embodiments, the length of the pull wire 42 may be between approximately 110-120 cm.

Upon distal advance of pull wire 42 to its limit of travel, an overlap 44 remains between the proximal end 36 of distal section 34 and the proximal section 33. This overlap 44 is configured to provide a seal to enable efficient transmission of vacuum from proximal section 33 to distal section 34. In some embodiments, the length of the pull wire 42 may be limited to ensure that there is a minimal overlap 44 between the proximal segment 33 and the distal segment 34 when the pull wire 42 is fully inserted into the proximal segment 33 or attached manifold in a distal direction. In some embodiments, the length of the proximal segment 33 may be sufficiently long for neurovascular applications such that when the proximal segment is positioned in a relatively proximal position (e.g., the horizontal petrous segment), the neuroanatomy effectively limits the distance by which the distal segment 34 may be extended, ensuring a sufficient overlap 44. For example, the distal segment 34 may not be able to extend further than the M2 segment of the middle cerebral artery (MCA) given its dimensions. Overlap 44 may be provided with any of a variety of additional features to facilitate a seal, such as a gasket, coating or tightly toleranced sliding fit, as described elsewhere herein. In some embodiments, the proximal end of the distal segment 34 may be slightly expanded to create a seal. For instance, the outer diameter of the proximal end of the distal segment 34 and the inner diameter of the proximal segment 33 may both be about 0.088 inches. Preferably the clearance between the OD of the distal section 34 and ID of the proximal section 33, at least in the vicinity of transition 32, will be no more than about 0.005 inches and preferably no more than about 0.003 inches to provide an effective seal in a blood environment. A larger clearance may be more feasible in embodiments comprising a sealing feature as described elsewhere herein.

Following positioning of the distal end of proximal section 33 within the vasculature, such as within the cervical carotid artery, the control 24 is manipulated to distally advance distal section 34 deeper into the vasculature. For this purpose, the pull wire 42 will be provided with sufficient column strength to enable distal advance of the distal tip 38 as will be discussed below.

The pull wire 42 and distal section 34 may be integrated into a catheter as illustrated in FIGS. 1 and 2. Alternatively, distal section 34 and pull wire 42 may be configured as a stand-alone catheter extension device as is discussed in greater detail below. The catheter extension device may be introduced into the proximal end of proximal section 33 after placement of proximal section 33 and advanced distally there through as illustrated in FIG. 3A, to telescopically extend the reach of the aspiration system.

Referring to FIG. 3B, the pull wire 42 may comprise a tubular wall having an axially extending central lumen 45. The central lumen 45 permits introduction of media such as lubricants, drugs, contrast agents or others into the distal section 34. In addition, the central lumen 45 extending through pull wire 42 permits introduction of an agitator as is discussed in greater detail below. As shown in FIG. 3B, the central lumen 45 may open into the lumen 40. The distal opening of the central lumen 45 may be positioned at a point along the length of the distal section 34 such that the central lumen 45 terminates where the lumen 40 begins (the distal opening of central lumen 45 may be longitudinally aligned with the proximal opening of lumen 40). The proximal opening of lumen 40 may be angled or slanted as shown in FIG. 3B. In some embodiments, the opening of lumen 40 may be flat. The distal opening of central lumen 45 may be flat as shown in FIG. 3B. In some embodiments, the opening may be angled or slanted, similar to the opening of lumen 40 in FIG. 3B.

In some embodiments, the central lumen 45 may terminate proximal to the opening of the lumen 40. In some embodiments, the central lumen 45 may terminate distal to the opening of the lumen 40 and/or the proximal end of the distal section 34 (e.g., at a point within the lumen 40). For example, the central lumen 45 may terminate at the distal end of the distal section or just short of the distal end (e.g., no more than approximately 1 cm from the distal end). In some implementations, the portion of the pull wire 42, with or without a central lumen 45, which extends beyond the proximal end of the distal section 34 (e.g., into lumen 40) may decrease in stiffness (durometer) in a distal direction. The pull wire 42 may be relatively stiff along the portion proximal to the proximal end of the distal section 34 in order to provide sufficient pushability of the extension catheter. The stiffness of the portion of the pull wire 42 distal of the proximal end of the distal section 34 may substantially match or be less than the stiffness of the distal section 34 along the length of the distal section 34. The portion of the pull wire 42 distal of the proximal end of the distal section 34 may have a uniform stiffness less than the stiffness of the portion proximal of the proximal end of the distal section 34 or it may have a gradated or gradually decreasing stiffness in the distal direction, decreasing from the stiffness of the portion proximal of the proximal end of the distal section 34. For example, the pull wire 42 may comprise metal along the portion proximal to the proximal end of the distal section 34 and may comprise a polymer, softer than the metal, along the portion distal to the proximal end of the distal section 34. The portion distal to the proximal end, in some embodiments, may be extruded with decreasing stiffness in the distal direction.

Disclosed herein are various embodiments for sealing an annular gap between an inner device 3402, such as a tube or catheter, and an outer device 3404, such as a tube or catheter. The inner device 3402 may be the axially translatable distal section 34 of the tubular body 16 of catheter 10 and the outer device 3404 may be the fixed proximal section 33 of the tubular body 16 of catheter 10. The inner device 3402 and the outer device 3404 may form a sealed extendable catheter device 3400. The device 3400 may be sealed within an area of overlap, such as the overlap 44 between the proximal section 33 and the distal section 34 by a sealing feature or mechanism 3406. See FIG. 3B Providing a sealing feature 3406 between the proximal section 33 and the distal section 34 may advantageously provide a seal, and eliminate or reduce the volume of space and/or surface area of device that can act as a stagnation zone for blood that is drawn into the annular gap, which may help reduce or mitigate thrombogenesis. See FIG. 4. Mitigating the opportunity for thrombogenesis to occur may help prevent formation of emboli resulting from the intravascular treatment. It is to be understood that sealing features 3406 disclosed herein may just as suitably apply to an extendable device in which the inner device 3402 is fixed and the outer device 3404 is extendable/retractable relative to the inner device 3402.

Figure 4:
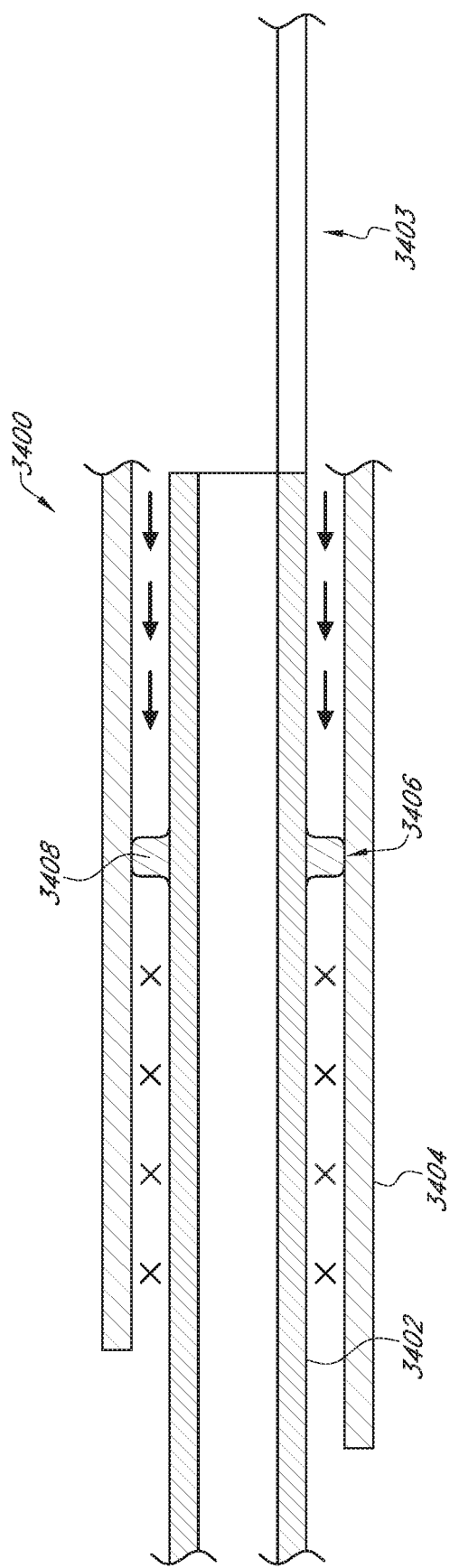
FIG. 4 schematically illustrates a device comprising an inner catheter extendable through an outer catheter in which a protrusion serves as a sealing feature for sealing an annular gap between the inner catheter and the outer catheter.

In some embodiments, the sealing feature 3406 may be a protrusion 3408 extending from either the outer surface of the inner device 3402 (e.g., an expanded diameter section) or the inner surface of the outer device 3404 (e.g., a reduced diameter section). The protrusion 3408 may form a ring or ring-like annular feature around the outer surface of the inner device 3402 or the inner surface of the outer device 3404. As used herein, "annular" merely requires that the sealing feature extend all the way or substantially all the way around the inner device, sufficient to achieve the sealing function. However it does not require that the seal reside within a single transverse plane as shown in FIG. 4. Annular rings may also reside on a plane that is angled other than 90° from the longitudinal axis, such as for example shown in FIGS. 7 and 8.

The protrusion 3408 may operate by forming a close or slight interference sliding fit with the opposing device (the outer diameter of the inner device 3402 or the inner diameter of the outer device 3404). FIG. 4 schematically illustrates a cross section of a device 3400, which may comprise the same or similar features as device 10 described elsewhere herein, comprising a single protrusion 3408 extending from the inner device 3402. The protrusion 3408 may comprise an outer diameter substantially equal to the inner diameter of the outer device 3404. The protrusion 3408 may comprise an outer diameter slightly larger than the inner diameter of the outer device 3404 but be compliant enough such that the outer device 3404 radially compresses the protrusion 3408 in order to accommodate the protrusion 3408 forming a sliding fluid seal in the process.

As shown in FIG. 4, the protrusion 3408 prevents or inhibits blood flow which may enter the annular gap between the inner device 3402 and the outer device 3404 from flowing proximally past the protrusion 3408. In some implementations, the annular gap may be flushed with a solution in the volume proximal to the protrusion 3408. The solution may be saline. The solution may contain heparin and/or another anticoagulant which helps reduce the risk of thrombogenesis. The flushing solution may be particularly beneficial for washing the surfaces of the inner device 3402 and/or outer device 3404 along a length that was previously exposed to blood flow when the inner device 3402 and protrusion 3408 were in a retracted position, once the device is in a relatively extended position such that the protrusion 3408 is now positioned distally of that length of the outer device 3404. If the inner device 3402 is subsequently retracted again such that the protrusion 3408 is now positioned proximally to that previously exposed length of device, the flushing solution, particularly one comprising an anticoagulant, will reduce the risk that any thrombus, or activated coagulation factors, will be re-exposed to the blood stream.

In some embodiments, the protrusion 3408 may prevent the flushing solution from flowing distally beyond the protrusion 3408 (distal or antegrade flow). In some embodiments, the protrusion 3408 may act as a one-way valve allowing distal flow but not fluid flow proximally past the protrusion 3408 (proximal or retrograde flow). The protrusion 3408 may be shaped or otherwise constructed to more easily bend in a distal direction than in a proximal direction to achieve a one-way valve effect. In some embodiments, the protrusion 3408 may be configured to allow distal fluid flow only upon surpassing a threshold fluid pressure. A flushing fluid could be continually maintained proximal the protrusion 3408 and forced to flow past the protrusion 3408 on demand by increasing the fluid pressure, such as with a syringe or other control at a proximal end of the device 3400. The flushing fluid may be provided through a separate tube or lumen which is configured to extend into the annular gap.

The flushing fluid may be provided at times when aspiration is not provided through the catheter 10 or the flushing fluid may be provided contemporaneously with aspiration. The flushing fluid may flush the portion of the gap proximal to the protrusion 3408 and be aspirated via the aspiration provided through the catheter 10. In some implementations, the pressure of the flushing fluid may be sufficient to overpower the suction pressure, at least transiently, and force the one-way fluid seal open to distal flow to flush the portion of the annular gap distal to the protrusion 3408. In some embodiments, flushing fluid may be provided through the entire catheter 10 so as to flush through the inner device 3402, the outer device 3404, and the annular gap between the inner device and outer device, at times when aspiration is not provided through the catheter.

Figure 5:
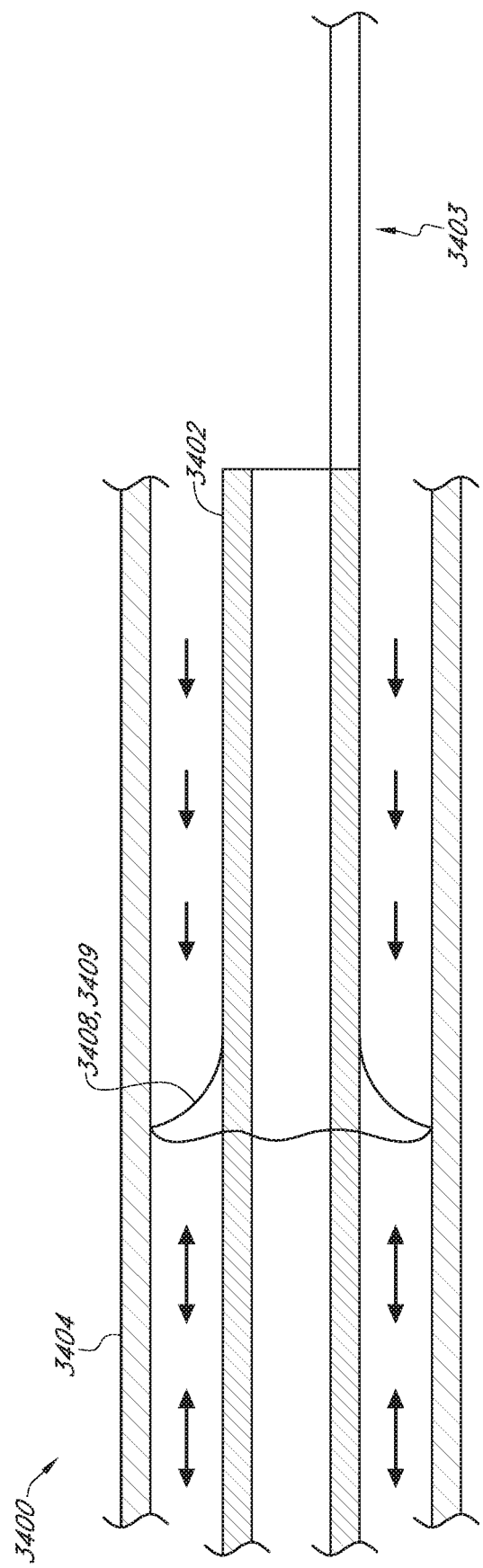
FIG. 5 schematically illustrates a device comprising a skirt shaped protrusion or flange for creating a one-way valve to seal the annular gap.

FIG. 5 schematically illustrates a device 3400 comprising a skirt-shaped protrusion 3408. The skirt-shaped protrusion 3408 may comprise an annular conical flap 3409 which extends radially outward from the inner device 3402 and distally. The flap 3409 may be compliant enough to deform in a distal direction under the pressure of the flushing solution, bending toward the axis of the inner device 3402, in order to allow distal fluid flow. The flap 3409 may be forced under pressure from the proximal blood flow and/or aspiration to deform or extend in a more radial direction, normal to the longitudinal axis of the inner device 3402, so as to form a tighter seal with the outer device 3404. In some embodiments, the annular protrusion 3408 may comprise a non-uniform stiffness around the circumference of the protrusion 3408. For instance, certain segments of the circumference may be softer or more compliant than other segments forming flaps 3409 or one-way valves while other portions of the circumference may be sufficiently rigid such that neither distal nor proximal fluid flow is permitted.

The protrusion 3408 may be the same material or a different material as the portion of the device (e.g., tubular body 16) from which it extends. In some embodiments, the protrusion 3408 may comprise polyether block amide (e.g., PEBAX®), polyethylene, polyurethane, Tecothane®, nylon, etc. In some embodiments, the protrusion 3408 may be formed from a softer material than the inner device 3402, or at least an outer layer (e.g., an outer jacket) of the inner device 3402. In some embodiments, the protrusion 3408 may be formed from a softer material than the outer device 3404 or at least an inner layer (e.g., an inner liner) of the outer device 3404. For example, the protrusion 3408 may be formed as part of an outer jacket of the inner device 3402. In some embodiments, the protrusion 3408 may be coextruded with the outer jacket.

In some embodiments, the protrusion may be adhered to the outer jacket, such as with a biocompatible adhesive, melted onto the outer jacket, molded onto the outer jacket, or otherwise adhered to the outer diameter of the inner device 3402. In some embodiments, the protrusion 3408 may be formed by a discrete tubular segment of the outer jacket having a larger outer diameter than two adjacent segments of the outer jacket which the protrusion 3408 is positioned between. In some embodiments, the protrusion 3408 may be formed as an expanded diameter portion of a tubular segment of the outer jacket. In some embodiments, the protrusion 3408 may be solid throughout. In some embodiments, the protrusion 3408 may be at least partially hollow, which may increase the flexibility of the protrusion 3408.

The protrusion 3408 may have a cross-section along its circumferential axis (around the outer diameter of the outer device 3404) of any suitable shape. For example, the cross-section may be rectangular, square, rounded, triangular, etc. The cross-section may be symmetric or asymmetric about a proximal-to-distal midline. The protrusion 3408 may comprise a proximal surface and a distal surface. In some embodiments, the distal surface may be convex, concave, and/or substantially flat. In some embodiments, the proximal surface may be convex, concave, and/or substantially flat.

The proximal surface and distal surface may have different degrees of stiffness or flexibility. For example, the proximal surface may more easily bend to produce a one-way valve effect as described elsewhere herein. The protrusion 3408 may be shaped with a hinge feature (e.g., a divot in the distal surface) that allows fluid flow in the distal direction but not the proximal direction. Thinner portions of the cross section may be more flexible than thicker portions of the cross-section. In some embodiments, the cross-section may thin-out towards the outer diameter of the protrusion 3408 to facilitate bending of the protrusion 3408 near the point of contact with the outer device 3404 and axial translation of the sealing protrusion 3408 along the inner surface of the outer device 3404.

In some embodiments, the protrusion 3408 or other sealing feature 3406, as described elsewhere herein, may be positioned on an inner surface of the outer device 3404. The protrusion 3408 may be fabricated in the same or similar manner (e.g., from the inner liner of the outer device 3404). In some embodiments, both the inner device 3402 and the outer device 3402 may comprise protrusions 3408 or other sealing feature 3406. A protrusion 3408 on the outer device 3404 may be positioned to be proximal to, distal to, or axially aligned with a protrusion 3408 on the inner device 3402 when the extendable device 3400 is in a fully extended position or when the extendable device 3400 is in a fully retracted position. A protrusion 3408 on the inner device 3402 may be configured to axially cross over a protrusion 3408 on the outer device 3404 as the inner device 3402 is axially translated relative to the fixed outer device 3404, or the inner device 3402 and outer device 3404 may be configured such that the protrusions 3408 remain in their respective proximal/distal spatial relationships. In some embodiments, protrusions 3408 on the inner device 3402 and the outer device 3404 may be configured to serve as stops that abut one another and limit axial translation of the inner device 3402 with respect to the outer device 3404 in a distal and/or proximal direction.

Figure 6:
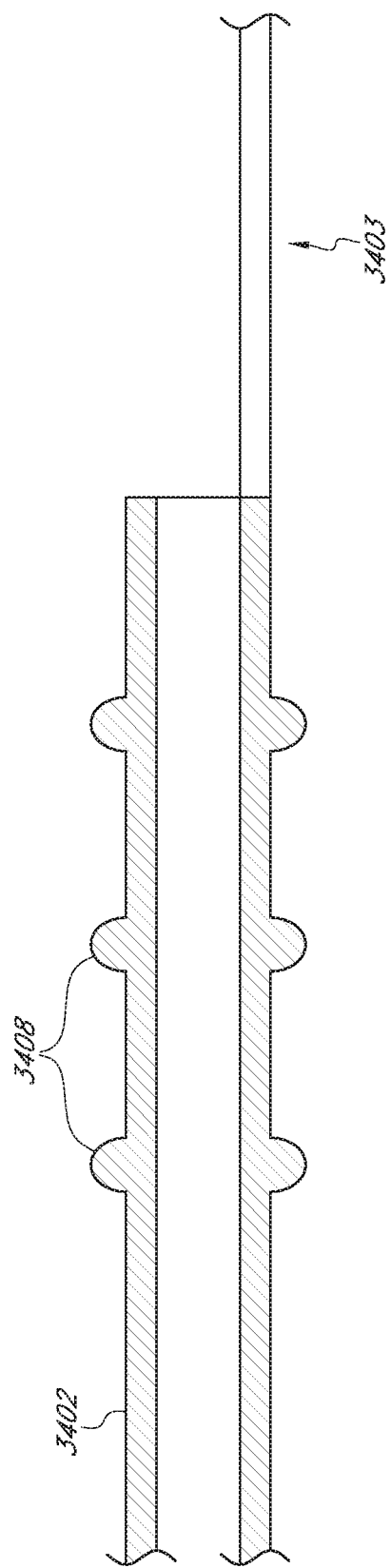
FIG. 6 schematically illustrates an inner device comprising multiple protrusions.

The inner device 3402 may contain one or more protrusions 3408 (e.g., 1, 2, 3, 4, 5, etc.) and/or the outer device 3404 may contain one or more protrusions 3408 (e.g., 1, 2, 3, 4, 5, etc.). FIG. 6 schematically depicts an inner device 3402 having multiple axially spaced protrusions 3408 or multiple revolutions of one or two or more helical protrusions spiraling or positioned along a proximal end of the inner device 3402. In devices 3400 in which the inner device 3402 and the outer device 3404 comprise protrusions 3408 and at least one of the inner or outer devices 3402, 3404 comprises multiple protrusions 3408, the protrusion 3408 may be arranged in any combination of the spatial relationships described elsewhere herein. For example, the inner device 3402 may comprise a protrusion 3408 surrounded on its proximal and distal sides by protrusions 3408 on the outer device 3404 or vice-versa. The inner device 3402 may comprise a protrusion 3408 and the outer device 3404 may comprise multiple protrusions 3408 positioned proximally and/or distally of the protrusion 3408 on the inner device or vice-versa. Some or all of the protrusions 3408 on the inner device 3402 may be positioned to be axially translatable over some or all of the protrusions 3408 on the outer device 3408 or vice-versa.

In some embodiments, one or more protrusions 3408 on the inner device 3402 may be configured to extend distally beyond the distal end of the outer device 3404, such as in a fully extended configuration. In some embodiments, one or more protrusions 3408 on the inner device 3402 may be configured not to extend distally beyond the distal end of the outer device 3404 such that they remain within the annular gap, such as in a fully extended configuration. In some embodiments, one or more protrusions 3408 on the outer device 3404 may be configured to extend proximally beyond the proximal end of the inner device 3402, such as in a fully extended configuration. In some embodiments, one or more protrusions 3408 on the outer device 3404 may be configured not to extend proximally beyond the proximal end of the inner device 3402, such as in a fully extended configuration.

In some embodiments, the protrusion 3408 may be uniformly distributed around the circumference of the inner device 3402 or outer device 3404 at a given axial position along the length of the inner device 3402 or outer device 3404, forming a simple ring defining a transverse plane that is 90° from the longitudinal axis of the catheter. In other embodiments, the protrusion 3408 may incline in an axial direction as it circumnavigates the outer circumference of the inner device 3402 or the inner circumference of the outer device 3404. For example, the protrusion 3408 may shaped as an annular circle (90° to the longitudinal axis), oval (inclined at an angle other than 90°), diamond, or other suitable shape that is slanted along the axial direction such that the protrusion 3408 forms a proximal tip 3408a and/or a distal tip 3408b.

Figure 7A:
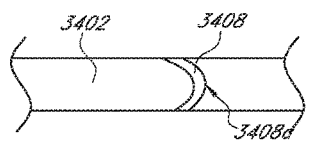
FIGS. 7A-7F schematically illustrate various examples of side views of slanted protrusions which extend at an angle along the axial length of the inner catheter.
Figure 7C:
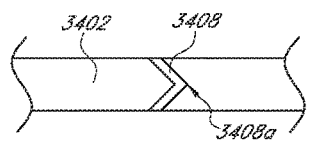
Figure 7E:
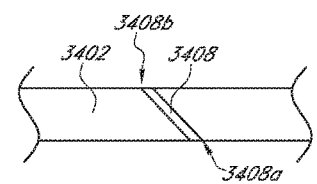
Figure 7B:
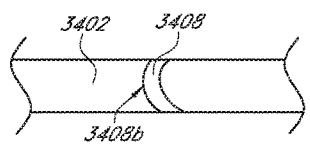
Figure 7D:
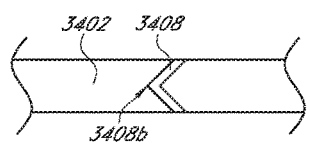

FIGS. 7A-7F schematically illustrate side views of various configurations of inclined or angled protrusions 3408. In some embodiments, the slanted protrusion 3408 may form a rounded proximal and/or distal edge as shown in FIG. 7A, showing a proximal tip 3408a. FIG. 7B, showing a distal tip 3408b rotationally offset from the proximal tip 3408a.

Figure 7F:
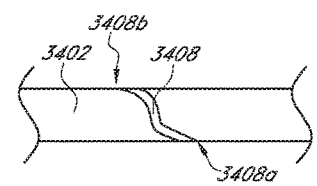

In some embodiments, the slanted protrusion may form a pointed tip as shown in FIG. 7C, showing the proximal tip 3408a, and 7D, showing the distal tip 3408b, in which the tips comprise a chevron-shaped profile. The views in FIGS. 7A and 7C may be substantially rotationally opposite the views in FIGS. 7B and 7D, respectively, such that the proximal tip 3408a and the distal tip 3408b are positioned on substantially opposite sides of the inner device 3402. FIGS. 7E and 7F show examples of side views which may be approximately 90 degrees offset from the views in FIGS. 7A-7D.

Protrusions 3408 may comprise any combination of the views and shapes depicted as well as other shapes. For example, in some embodiments, the protrusion 3408 may comprise a rounded proximal tip 3408a and a pointed distal tip 3408b or vice versa. In some embodiments, the protrusion may comprise a proximal tip 3408a but no defined distal tip 3408b (e.g., the protrusion is distributed evenly around at least a portion of the circumference at its distal end) or vice versa. The configuration of the slanted protrusions 3408, particularly the chevron-shaped profiles, may reduce the force required to axially translate the inner device 3402 relative to the outer device 3404, while maintaining a sealed space.

Figure 8A:
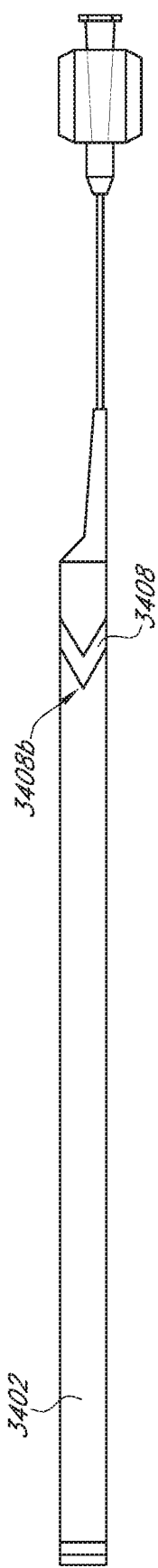
FIGS. 8A-8E schematically illustrate side views of two examples of inner catheters which comprise a chevron-shaped protrusion for sealing the device.
Figure 8B:
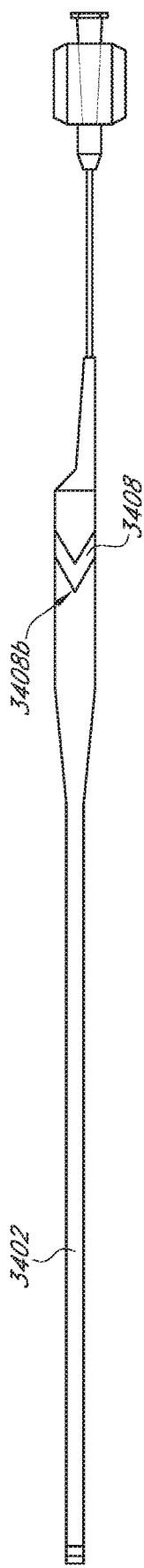
Figure 8C:
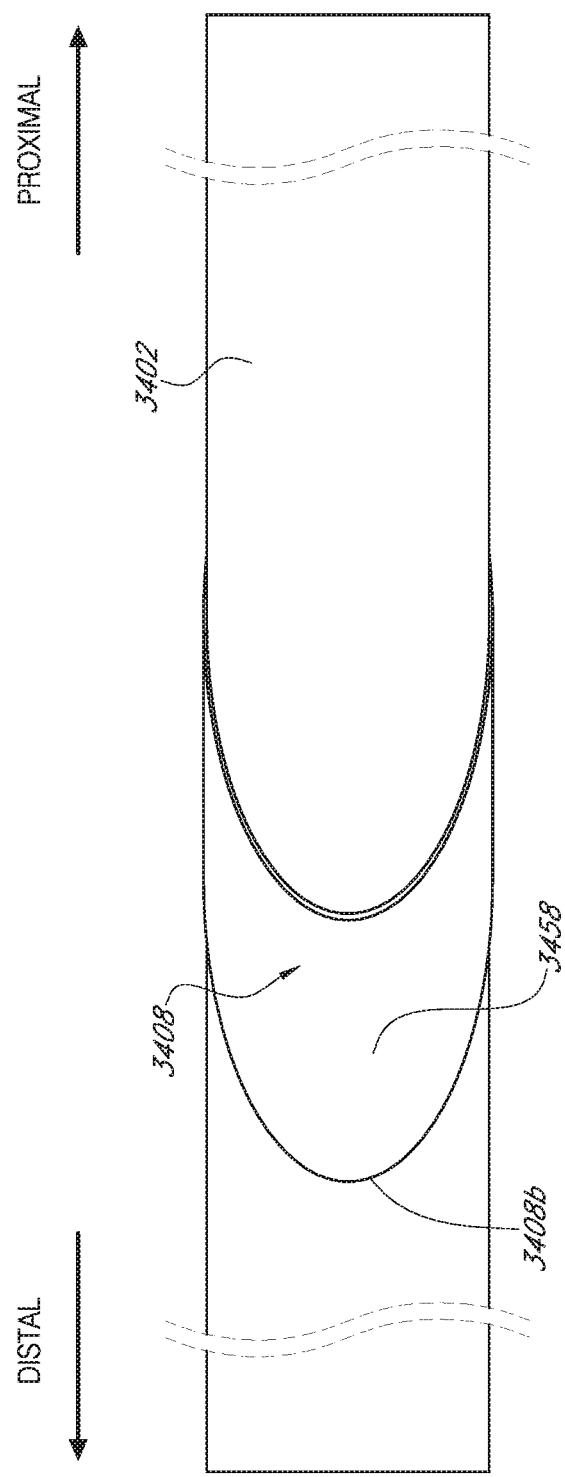
Figure 8D:
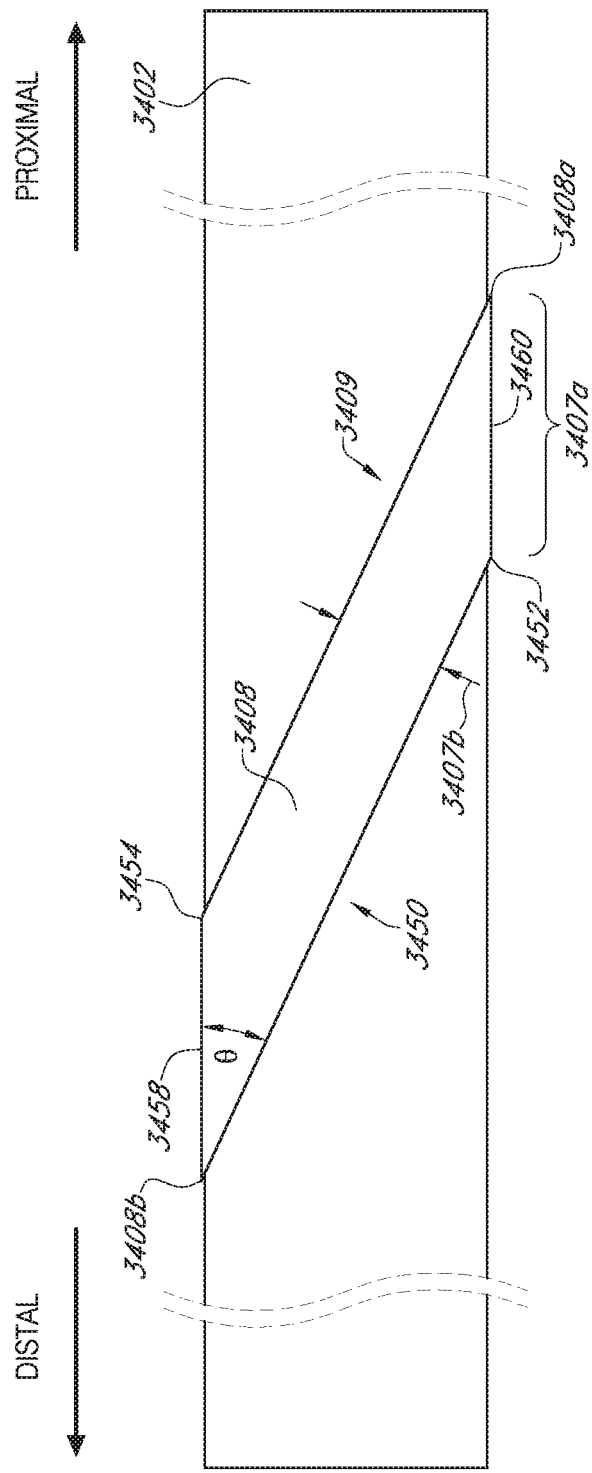
Figure 8E:
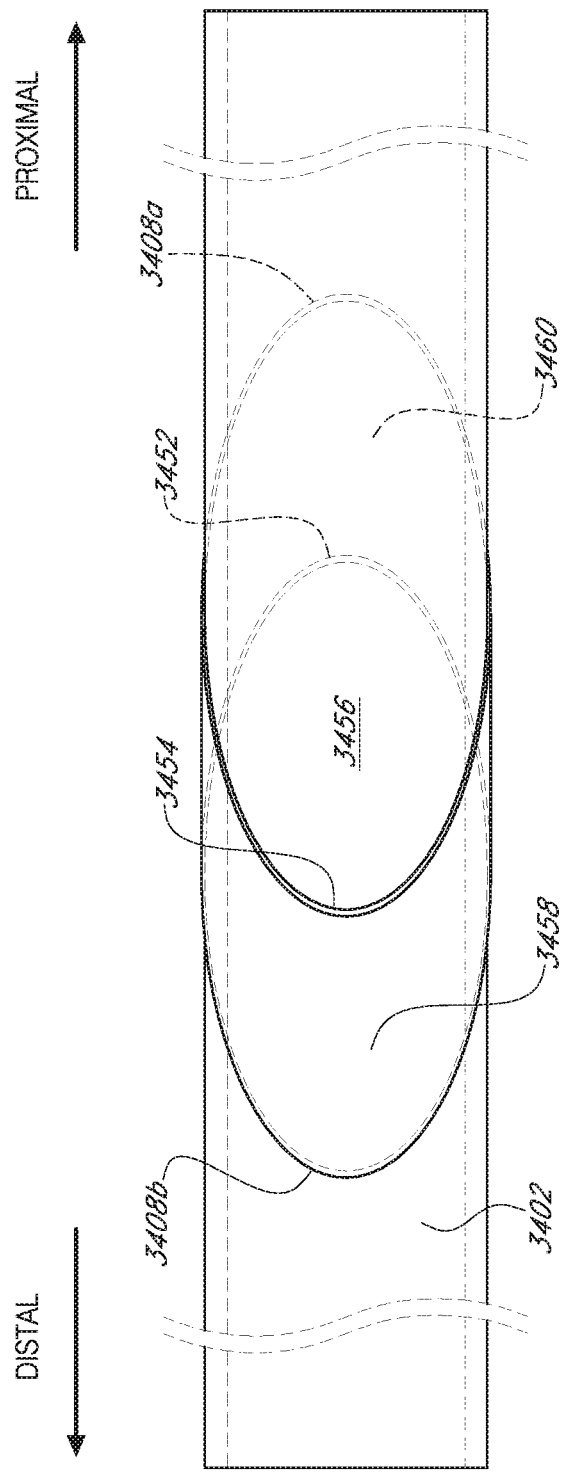

FIGS. 8A and 8B schematically illustrate two examples of a spined catheter inner device 3402, similar to those described elsewhere herein, in which a proximal end of the catheter extension tube portion of the device 3402 comprises a chevron-shaped protrusion 3408. The tubular body 3400 in FIG. 8A comprises a constant internal diameter, which may be approximately 0.71 inches. The device 3400 in FIG. 8B comprises an expanded diameter portion at the proximal end, which may have an internal diameter of about 0.71 inches, and transitions to a reduced diameter portion near the distal diameter, which may have an inner diameter of approximately, 0.35 inches, 0.45 inches, 0.55 inches, or any diameter in a range defined there between. FIGS. 8C-8E illustrate close-up views of an example of chevron-shaped protrusions 3408 on the inner device 3402. The view in FIG. 8D is approximately 90 degrees offset around the circumference of the inner device 3402 from the view in FIG. 8C. FIG. 8E is a view like FIG. 8C, but also showing the orientation of the protrusion on the back side of the catheter.

As shown in FIG. 8D, the protrusion 3408 may comprise dimensions including a width 3407a in an axial direction and an angle θ defined relative to the longitudinal axis of the inner tubular body 3402. In some embodiments, the width 3407a of the protrusion 3408 may be substantially constant around the circumference of the inner device 3402. For example, the width 3407a may be between approximately 0.01 and 0.3 inches, 0.02 and 0.2 inches, 0.03 and 0.1 inches, 0.035 and 0.08 inches, 0.04 and 0.06 inches, or 0.045 and 0.055 inches. In some embodiments, the width 3407a may be larger at and/or near the proximal trailing tip 3408a and/or the distal leading tip 3408b of the protrusion 3408, as shown in FIG. 8C. For example, the width 3407a at these points may be approximately 1.5×, 1.75×, 2×, 2.25×, 2.5×, 2.75×, 3×, 3.25×, 3.5×, 3.75×, 4×, 4.25×, 4.5×, 4.75×, or 5× larger than the width 3407b at a point where it is the smallest (e.g., halfway between the proximal point 3408a and the distal point 3408b).

For instance, in some embodiments, the width 3407a near the proximal point 3408a and/or the distal point 3408b may be between approximately 0.05 and 0.3 inches, 0.1 and 0.2 inches, or 0.11 and 0.13 inches. The width 3407a may vary in a continuous pattern across the circumference of the inner device 3402.

In some embodiments, the angle θ may be defined via a straight line connecting the proximal tip 3408a to a point 3452 on the proximal edge opposite the distal tip 3408b or connecting the distal tip 3408b to a point 3452 on the distal edge opposite the proximal tip 3408a, which in the illustrated embodiment lies on a proximal edge 3409 of the inclined seal. In some embodiments, the angle θ may be defined by a best fit straight line along the proximal and/or distal edge of the protrusion, in the case of nonlinear edges. The other examples of protrusions 3408 disclosed herein may have the same or similar dimensions.

In some embodiments, the trailing and/or leading edge of the protrusion 3408 may form an angle θ relative to the longitudinal axis that is no larger than about 10 degrees, 15 degrees, 20 degrees, 25 degrees, 30 degrees, 35 degrees, 40 degrees, 45 degrees, 50 degrees, 55 degrees, or 60 degrees. In some embodiments, the angle θ may be between about 15 and 45 degrees, 20 and 40 degrees, 20 and 30 degrees, or 30 and 40 degrees. Protrusions 3408 having a lower angle θ may facilitate sliding of the inner device 3402 within the outer device 3404 in an axial direction.

The illustrated protrusion 3408 is in the form of an inclined annular seal having a distal edge 3450 on the opposite axial end of the seal from proximal edge 3409. The distal edge 3450 may reside on a plane that is substantially parallel to the proximal edge 3409 in an embodiment having a constant thickness 3407a, both of which are non perpendicular to the longitudinal axis of the catheter.

The inclined distal edge 3450 has a first, distal transition or limit at leading point 3408b and a second, proximal limit 3452 which is axially proximally offset from the first distal limit by at least about 2 mm; at least about 3 mm or 4 mm or more.

The inclined proximal edge 3409 extends between a distal limit 3454 and a proximal limit 3408a. As a result of the axial offset and width 3407a of the protrusion 3408, a window 3456 may be formed between the distal limit 3454 and proximal limit 3452 of the opposing edges of the seal depending upon the incline angle of the seal. See FIG. 8E. A distal sliding surface 3458 is thus axially offset from a proximal sliding surface 3460 by an amount that corresponds to the axial length of the window 3456. In the illustrated embodiment, the window 3456 has a major axis extending in the catheter longitudinal axis direction. At any point within the window, a line can be drawn transverse through the catheter without intersecting the protrusion 3408.

The window 3456 may have a major axis within the range of from about negative 0.5 mm (slight axial overlap of the distal sliding surface 3458 and proximal sliding surface 3460) to about 4 mm, and in some implementations at least about 1 mm or 2 mm and in some cases within the range of from about 2 mm to about 3 mm. The major axis of the window 3456 is about 2.6 mm in one implementation having a seal width 3407a of about 2 mm and a catheter OD of about 0.086 inches.

An end view of the distal edge 3450 and or proximal edge 3409 taken along a viewing axis that is perpendicular to the plane of the respective edge can define an ellipse. In one implementation, the ellipse dimensions are 0.086" in the minor axis direction, which is equal to the OD of the catheter. The ellipse is about 0.2057" in the major axis direction, about 2 to 2.5 times the catheter diameter. This means the seal inclines at about 30 degrees to the long axis of the catheter. At an incline of about 15 degrees the long axis increases to almost 4 times the catheter diameter. This is rather steep and may be a reasonable limit. At the other extreme a 75 degree angled seal (almost straight across) would not have sufficient axial offset of the opposing sliding surfaces, (desirable to minimize drag) if the seal width was 25% or less of the catheter diameter. This would be an ellipse ratio of only about 1.03. As the seal gets wider, the minimum ratio would climb with the angle dropping off. Thus, ellipse major axis dimensions within the range of from about 1.25 to about 4 times the minor axis dimension will typically be used, often within the range of from about 1.5 to about 3×× the minor axis dimension.

Preferably, the trailing edge 3454 (inside the ellipse) of the seal on one side should overlap minimally, or ideally not at all with the leading edge 3452 (inside of the ellipse) of the seal on the opposite side.

As a consequence of the angled nature of the annular seal, the overall length in the catheter axial direction from distal tip 3408b to proximal tip 3408a will often be at least about 1.5 times or two times the width 3407a. In some implementations, the overall tip to tip length may be at least about 2.5 times or 3 times the width 3407a. Multiples within the range of from about 1.5 times and about 5 times, or from about 2 times and about 3.5 times may be utilized depending upon desired performance. In one implementation having a width 3407a of about 2 mm and a catheter OD of about 0.086 inches, the overall axial length from tip to tip is between about 4 mm and about 8 mm, between about 6 mm and about 7 mm and optionally about 6.7 mm.

The overall length may be elongated further by introducing an axial extension segment on each side of the catheter such as at about the midpoint between proximal tip 3408a and distal tip 3408b. In this implementation the distal edge 3450 for example would not appear as it does in side elevational view (FIG. 8D) to be a linear edge between 3408a and 3408b. Instead, a distally facing segment extending proximally from point 3408b and a distally facing segment extending distally from point 3408a would be separated by a central segment facing a different angle such as laterally in the case of an axially extending central extension segment.

The chevron configured seal allows for effective sealing inside another tube by not requiring the other (outer) tube to have a friction fit around a full 360 degrees at the same axial location transverse plane. The contact points of the chevron allow the inner and outer tubes to be inclined slightly to each other to relieve the friction of the sealing surface and at the midpoint of the chevron the outer tube can ovalize slightly while never allowing a leak path to form.

The protrusions 3408 disclosed herein may be any suitable thickness. For example, the protrusions 3408 may be no greater than approximately 0.01 mm, 0.025 mm, 0.05 mm, 0.075 mm, 0.1 mm, 0.25 mm, 0.5 mm, 0.75 mm, 1 mm, 2 mm, 3 mm, 4 mm, 5 mm, less than 0.1 mm, more than 5 mm, or a thickness within a range defined there between. In some embodiments, the protrusions 3408 may have uniform thickness. In some embodiments, the thickness may be between about 0.001 and 0.005 inches, 0.0015 and 0.004 inches, or 0.002 and 0.003 inches. In some embodiments, the protrusions 3408 may have variable thickness as they extend circumferentially around the circumference of the inner device 3402 or outer device 3404. As described elsewhere herein, the protrusion 3408 may have an outer diameter that is substantially equal to the inner diameter of the outer device 3404. For example, both diameters may be between about 0.085 and 0.09 inches, 0.086 and 0.089 inches, or 0.087 and 0.088 inches. In some implementations, the outer diameter of the protrusion 3408 and the inner diameter of the outer device 3404 may vary by less than about 0.002 inches, 0.001 inches, or 0.005 inches.

In some embodiments, the protrusion 3408 may be formed from the same material as an outer layer of the inner device 3402, such as Pebax®. The protrusion may be formed by extruding the material in a similar way one or more layers of the inner device 3402 are formed. The extruded material may be cut (e.g., diagonally cut) to form the shape of the ring having dimensions 3407a and 3408b. In some embodiments, the protrusion 3408 may be positioned around the inner device 3402 and then heated to laminate the protrusion 3408 to the outer surface of the inner device 3402, such as in a hot box. In some embodiments, the protrusion 3408 may be adhered to the inner device 3402 using an adhesive, such as a biocompatible adhesive. In some implementations, the protrusion may be post-processed. For example, the protrusion may be shaped by heating in a mold. The mold may be a glass mold. The mold may have an inner diameter approximately equal to the inner diameter of the outer device 3404 or slightly larger. For example, the mold may have an inner diameter of about 0.088 inches to achieve a protrusion 3408 having a diameter of approximately 0.0874 inches.

In some implementations, the protrusion 3408 may be molded or otherwise processed prior to attachment of the protrusion 3408 to the inner device 3408. In some embodiments, the protrusion 3408 may be attached or formed near the proximal end of the inner device 3402 as described elsewhere herein. For example, the protrusion 3408 may be formed within 5 cm, 4 cm, 3 cm, or 2 cm from the proximal end of the inner tubular body 3402. In some embodiments, as described elsewhere herein, the protrusion 3408 may be attached or formed on the most proximal Pebax® segment (e.g. a 72D segment). The protrusion 3408 may be attached or formed distally to any proximal Vestamid® segments. When attached or formed near the proximal end of the inner device 3402, the protrusion may have a durometer that is the same or less than that of the inner device 3402 at the same location. For example, the protrusion 3408 may have a durometer between about 45D and 70D, 50D and 65D, or 55D and 60D. For instance, a 55D protrusion 3408 may be positioned around a 72D segment of the outer jacket of the inner device 3402.

In some embodiments, the protrusion 3408 may be a spiral that extends along an axial length of the inner device 3402 and/or the outer device 3404. In some embodiments, the spiral may terminate at either its distal end and/or proximal end in closed circumference rings or connect to closed circumference rings. In some embodiments, the spiral may terminate at its distal end and/or proximal end in an open configuration which may allow some blood to pass through a helical passage formed by the spiral. The spiral may nonetheless impede the flow of blood into the annular gap. In some implementations, the smaller the pitch of the spiral the larger the impediment the spiral may provide against blood ingress. Rotation of the inner device 3402 in a first direction, depending on the direction (e.g., right handed or left-handed) of the spiral, may cause the spiral to expel fluid in a distal direction while rotation in a second direction may draw in blood. Rotation in the first direction may be used to expel a flushing solution as described elsewhere herein.

In some embodiments, the sealing feature 3406 may be an active feature which expands or otherwise activates to seal the annular gap and/or which can be deactivated to allow flow through the annular gap. The sealing feature 3406 may be deactivated when the inner device 3402 and the outer device 3404 are axially translated relative to one another so as to allow easier movement (e.g., less friction). The sealing feature 3406 may be activated when the inner device 3402 and the outer device 3404 are being used in a fixed position, such as a fully retracted and/or fully extended position.

Referring to FIG. 9 the active sealing feature 3406 may be an expandable bulge 3410. In various embodiments, the expandable bulge 3410 may be activated via a connection extending through the central lumen 3401 of a spine 3403 of the inner device 3402, such as the lumen 45 extending through the pull wire 42 described elsewhere herein. The expandable bulge 3410 may be mechanically expandable. For example, as schematically illustrated in FIG. 9, the expandable bulge 3410 may be formed from a soft or compliant polymer, such as an elastomeric polymer. The soft expandable bulge 3410 may be formed such that in an inactivated or un-expanded state the outer profile of the expandable bulge 3410 is in a reduced profile configuration such as flush with or in-line with the outer diameter of the inner device 3402. For example, the inner device 3402 may comprise a reduced diameter recess for receiving the expandable bulge 3410. The expandable bulge 3410 may be ring-shaped or cuff-shaped. In some embodiments, the expandable bulge 3410 may replace an outer layer of the inner device 3410 (e.g., the outer jacket) over a small axial length of the inner device 3410. The expandable bulge 3410 may not be adhered or fixed to the outer diameter of the inner device 3402 or it may be partially fixed, such as at a proximal end of the expandable bulge 3410.

The expandable bulge 3410 may be coupled to the inner device 3410 in a manner that allows axial compression of the expandable bulge 3410 along the outer surface of the inner device 3402. In some embodiments, the outer diameter of the expandable bulge 3410 in an un-activated or un-expanded state may extend beyond the outer diameter of the inner device 3402 but may not extend to the inner diameter of the outer device 3404 such that it does entirely seal the annular gap. In other embodiments, the expandable bulge 3410 may be applied over a smooth portion of the outer circumference of the inner device 3402. The expandable bulge 3410 may be fixed, such as at a proximal end, to the inner device 3402.

As shown in FIG. 9, the expandable bulge 3410 may be positioned at a proximal end of the inner device 3402. The expandable bulge 3410 may be sandwiched between a portion of the outer jacket of the inner device 3410 and a proximal structure. The proximal structure may be, for example, a radiopaque ring for determining the location of the proximal end of the inner device 3402. A tension cable or wire 3411 may extend from a proximal end of the device 3400 to the expandable bulge 3410. The tension cable 3411 may attach to a distal end of the expandable bulge 3410. Proximal retraction of the tension cable 3411 may apply an axially compressive force to the expandable bulge 3410 which causes the axial length of the expandable bulge 3410 to be compressed and the radial diameter of the expandable bulge 3410 to expand. Full expansion of the expandable bulge 3410 may increase the outer diameter of the expandable bulge 3410 to a size such that it is compressed against the inner diameter of the outer device 3404 and forms a fluid seal with the inner diameter of the outer device 3404.

Providing a distally directed counterforce on the inner device 3402 such as by pushing on the inner device 3402 (e.g., pushing on the spine 3403 through which the tension cable 3411 extends) may facilitate expanding the expandable bulge 3410 without axially translating the inner device 3402 relative to the outer device 3402, such as pulling the inner device 3410 proximally along with the tension cable 3411. In other embodiments, the expandable bulge 3410 may be compressed by pushing on a push wire which may be connected to a proximal end of the expandable bulge 3410. The expandable bulge 3410 may be fixed to the inner device 3410 at a distal end of the expandable bulge 3402. The expandable bulge 3402 may be positioned at a distal end or intermediate portion of the inner device 3402.

In some embodiments, the expandable bulge 3410 may be expandable by non-mechanical means. For example, the expandable bulge 3410 may comprise a light-sensitive or electrosensitive material, such as a light-sensitive hydrogel and/or an electrosensitive hydrogel. An electric current or light may be passed through the lumen, which may serve as or may comprise an insulator or fiber optic cable. The hydrogel may expand upon the application of light and/or an electric current and may collapse upon removal of the stimuli or vice-versa. In some embodiments, the expandable bulge 3410 may be inflatable and the lumen may serve as a passage for providing pressurized fluid (e.g. a gas or liquid, such as saline) which serves to inflate the expandable bulge 3410. The expandable bulge 3410 may be inflated and deflated to a controllable extent by controlling the pressure applied to the inflating fluid.

Figure 10:
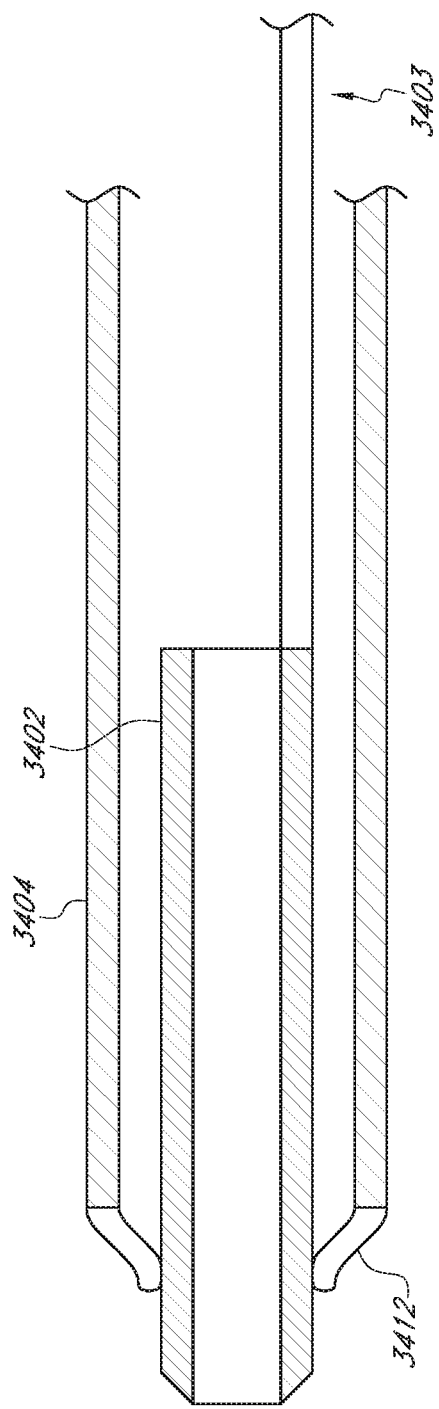
FIG. 10 schematically illustrates a device comprising a distal flange for sealing the annular gap.

In some embodiments, the sealing feature 3406 may comprise a flange 3412. FIG. 10 schematically illustrates an example of a device 3400 comprising a flange 3412. The flange 3412 may be annular in shape. The flange 3412 may be located at the distal end of the outer device 3404. In some implementations, the flange 3412 may comprise similar features as the protrusion 3408 described elsewhere herein. The flange 3412 may incline radially inward toward the inner device 3402 to form a frusto conical skirt configuration. In some embodiments, the flange 3412 may extend from an inner diameter of the outer device 3404. In some embodiments, the flange 3412 may be coupled to a distal face of the outer device 3404. The flange 3412 may comprise a soft and/or elastic material. The flange 3412 may be relatively softer and/or more flexible than the outer device 3404 or one or more layers of the outer device 3404 and/or relatively softer and/or more flexible than the inner device 3402 or one or more layers of the inner device 3402.

In some embodiments, the flange 3412 may be formed integrally with the outer device 3404. For example, the flange 3412 may be extruded as a part of an inner liner and/or a part of an outer jacket of the outer device 3412. In some embodiments, the flange 3412 may be the same material as a layer of the outer device 3412 but may be formed relatively thinner so that it is more flexible. In some embodiments, the flange 3412 may be formed as a separate component which is coupled to the outer device 3404. For example, the flange 3412 may be adhered to the outer device 3404 or melted or molded onto the outer device 3404. The flange may be a distal segment of an outer jacket of the outer device 3404. The flange 3412 may be relatively compliant. The flange 3412 may be configured to extend, in an unbiased configuration, radially inward in a substantially normal relation to the inner surface of the outer device 3404. The flange 3412 may be configured to extend, in an unbiased configuration, radially inward and somewhat in a distal direction such that it forms an oblique angle with the inner surface of the outer device 304.

The flange 3412 may comprise an inner diameter in an unbiased configuration which is smaller than the outer diameter of the inner device 3402. In some embodiments, the flange 3412 may be thicker along or near its outer diameter than along or near its inner diameter. In some embodiments, the flange 3412 may comprise uniform thickness. Extending the inner device 3402 past the distal end of the outer device 3404 may cause the flange 3412 to bend in a distal direction such that the inner diameter of the flange 3412 expands to accommodate the inner device 3404 and form a fluid seal along the outer surface of the inner device 3402 as shown in FIG. 10. An inner-most portion of the flange 3412 may deform to lie substantially flat against the outer surface of the inner device 3402. In some implementations, the flange 3412 may act like a squeegee along the outer surface of the inner device 3404. The flange 3412 may be made of a lubricious material and/or coated with a lubricious material to promote smooth translation of the inner device 3402 relative to the outer device 3404.

In some embodiments, the flange 3414 may maintain a flushing fluid proximal to the flange 3414 and/or may act as a one-way valve in the same manner as described with various configurations of the protrusion 3408 described elsewhere herein. Providing a flange 3414 or other sealing feature 3406 at a distal end of the outer device 3404 may advantageously maximize the volume of the annular gap which is sealed from the physiological environment. In some embodiments, the inner device 3402 may comprise a flange 3412 extending from its outer diameter in a radially outward direction, which may comprise features similar to the flange 3412 extending from the outer device 3402. For example, the outer diameter of the flange 3412 may be larger than the inner diameter of the outer device 3404. The flange 3412 may be positioned at a proximal end of the inner device 3402.

Figure 11:
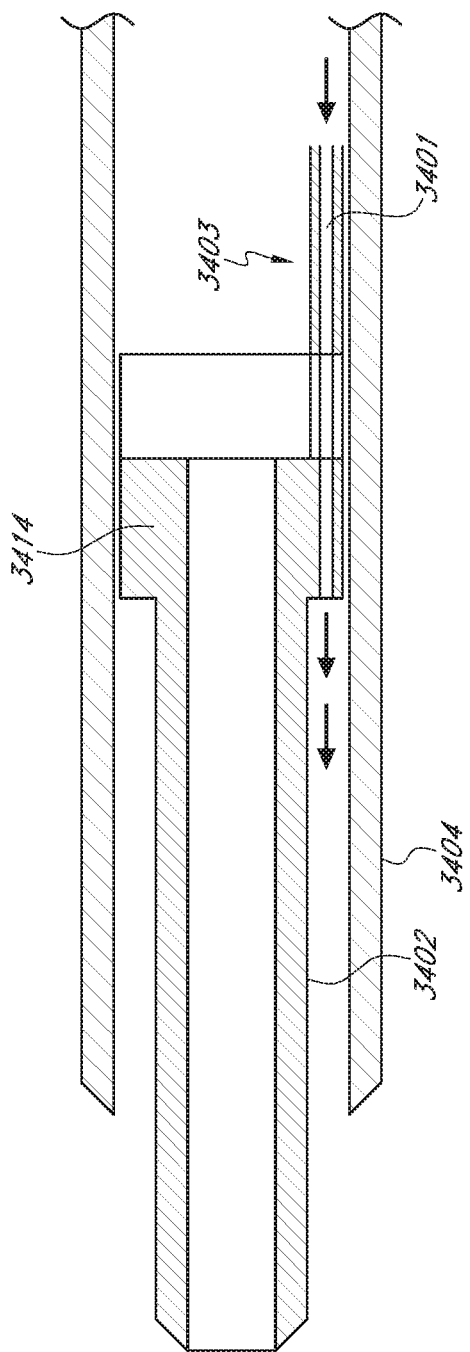
FIG. 11 schematically illustrates a device in which the inner catheter comprises a proximal hub for sealing the annular gap and in which a fluid port extends through the proximal hub.

In some embodiments, the sealing feature 3406 may comprise an expanded diameter portion of the inner device 3402, such as a hub 3414. FIG. 11 schematically illustrates an example of a device 3400 comprising a hub 3414. The hub 3414 may be configured to form a tight interference fit with the inner surface of the outer device 3404. The hub 3404 may prevent or reduce the amount of contact between a portion of the inner device 3402 distal to and/or proximal to the hub 3414 with the outer device 3404, which may reduce friction and facilitate translation of the inner device 3402 relative to the outer device 3404.

In some embodiments, the hub 3414 may comprise the same material as an outer jacket of the inner device 3404 or as any other layer of the inner device 3402. In some embodiments, the hub 3414 may be relatively softer and/or more flexible than the remaining length of the inner device 3402. In some embodiments, the hub 3414 may be relatively harder and/or stiffer than the remaining length of the inner device 3402. In some embodiments, the hub 3414 may comprise a uniform material extending between the non-expanded outer diameter of the inner device 3402 and the inner diameter of the outer device 3404. In some embodiments, the hub 3414 may comprise multiple layers between the non-expanded outer diameter of the inner device 3402 and the inner diameter of the outer device 3404. The layers may be of the same or different materials. In some embodiments, one or more outer layers may be softer, more flexible, and/or more lubricious than one or more inner layers. The outer layer or layers may facilitate smooth interaction with the outer device 3404 and the inner layers may provide structural support to the outer layers. In some embodiments, the hub 3414 may be positioned adjacent to a radiopaque ring as illustrated in FIG. 11, such as distally adjacent to the radiopaque ring.

In some embodiments, the inner device 3404 may comprise a spine 3403 (e.g., a hypotube spine) as described elsewhere herein. The spine 3403 may comprise a lumen 3401. The spine 3403 may be positioned along an outer-most diameter of the inner device 3402. The spine 3403 may merge with the hub 3414 as shown in FIG. 11. The lumen 3401 may extend through the hub 3414 and open on a distal face of the hub 3414. In some embodiments, the outer diameter of the lumen 3401 may be flush with the non-expanded outer diameter of the inner device 3402. In some embodiments, the outer diameter of the lumen 3401 may be entirely surrounded by portions of the hub 3414. In some embodiments, a portion of outer diameter of the lumen 3401 may be positioned along the outer diameter of the hub 3414, such that the lumen 3404 forms a groove along an outer surface of the hub 3414.

The hub 3414 may thereby comprise a distal port 3454 on a lumen extending through the seal which allows delivery of flushing fluid through the lumen 3401 across the seal and into the annular gap. Providing pressure from the proximal end of the lumen 3401 may allow delivery of flushing fluid while preventing proximal fluid flow through the port of the sealing feature 3406. In some embodiments, the lumen 3401 may extend linearly through the hub 3414 such that the port 3454 is collinear with the remainder of the lumen 3401. In some embodiments, the lumen may turn, such as in a circumferential direction, and/or branch off into multiple ports. Multiple ports may be positioned, for example, at different circumferential points around the hub 3414.

Figure 12A:
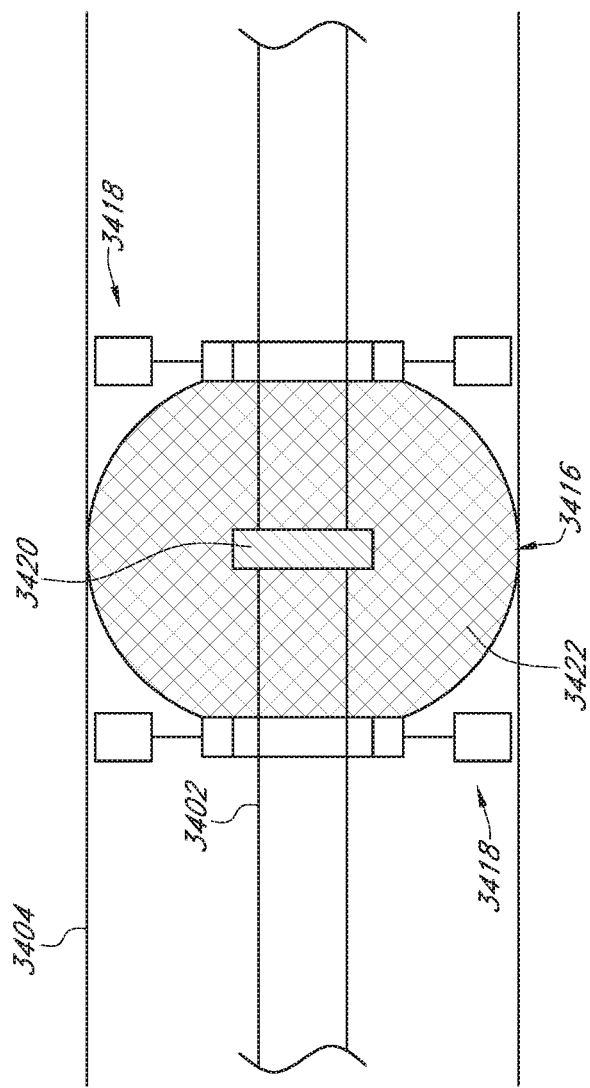
FIGS. 12A-12C schematically illustrate a device comprising a spring sealing feature in which axial translation of the inner catheter axially extends and radially contracts the spring sealing mechanism.
Figure 12B:
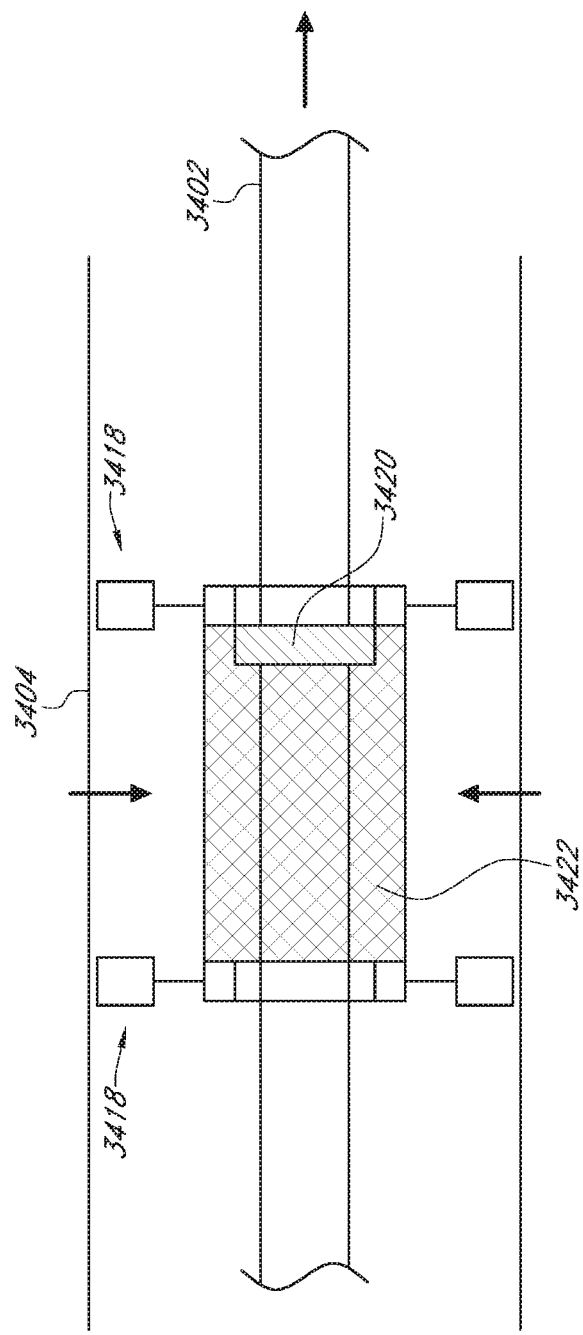
Figure 12C:
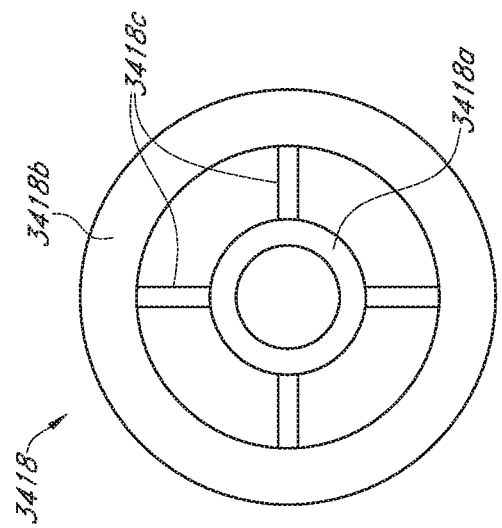

In some embodiments, the sealing feature 3406 may be dynamically responsive to movements of the inner device 3402 and/or outer device 3404. For example, the sealing feature 3406 may comprise spring devices which expand in an unbiased state and contract under force provided by movement of the inner device 3402, for example, and a counter frictional force between the inner device 3402 and the outer device 3404. FIGS. 12A-12C schematically illustrate an example of a device 3400 comprising a spring sealing feature 3416 which is radially compressed and axially extended by axial movement of the inner device 3402. FIG. 12A depicts the spring sealing feature 3416 in an axially compressed/radially expanded sealed configuration. FIG. 12B depicts the spring sealing feature 3416 in an axially extended/radially compressed non-sealed configuration. FIG. 12C depicts an example of a sliding ring 3418 used in the spring sealing feature 3416 of FIGS. 12A and 12B.

As shown in FIG. 12A, the inner device 3402 may be coupled to the outer device 3404 by two sliding rings 3418. One sliding ring 3418 may be positioned at a distal end of the spring sealing feature 3416 and one sliding ring 3418 may be positioned at a proximal end of the spring sealing feature 3416. As shown in FIG. 12C, the sliding ring 3418 may comprise an inner annulus 3418a, an outer annulus 3418b, and one or more spokes 3418c joining the inner annulus 3418a and the outer annulus 3418b. Multiple spokes 3418c may be positioned substantially uniformly around the circumference of the sliding ring 3418. Fluid may generally flow through the sliding rings 3418 between the spokes 3418c.

The inner annulus 3418a may be configured to form a sliding interference fit with the outer diameter of the inner device 3402. The outer annulus 3418b may be configured to form a sliding interference fit with the inner diameter of the outer device 3404. The inner annulus 3418a may have a first coefficient of friction with respect to the inner device 3402 and the outer annulus 3418b may have a second coefficient of friction with respect to the outer device 3404. The first and second coefficients of friction may be the same or one may be larger than the other. Although the outer annulus 3418 is shown as comprising a complete circumference in FIG. 12C, in some embodiments, the outer annulus 3418*b* may not extend around the complete circumference. The circumference of the outer annulus 3418*b* may be broken up into one or more partial arcuate sections, each section being connected to one or more spokes 3418*c*. Reducing the circumferential coverage of the outer annulus 3418*b* may decrease friction between the sliding ring 3418 and the outer device 3404 and promote easier sliding of the sliding ring 3418 over the inner surface of the outer device 3404. The inner device 3402 may comprise a ridge feature 3420 projecting from the outer surface of the inner device 3402. For example, the ridge feature 3420 may be a ring fixed to the outer surface of the inner device 3402. The ridge feature 3420 may be positioned between the proximal and distal sliding rings 3418. The ridge feature 3420 may be configured to abut a proximal side of the distal sliding ring 3418 and push the sliding ring 3418 in a distal direction along the inner surface of the outer device 3404. Likewise, the ridge feature 3420 may be configured to abut a distal side of the proximal sliding ring 3418 and push the sliding ring 3418 in a proximal direction along the inner surface of the outer device 3404.

The spring sealing feature 3416 may comprise one or more radially compressible support structures such as springs 3422 extending from around the circumference of the inner annulus 3418*a* of the proximal sliding ring 3418 to the inner annulus 3418*a* of the distal sliding ring 3418. For instance, the springs 3422 may comprise a plurality of spring struts extending parallel to a longitudinal axis of the device 3400 from one sliding ring 3418 to another. The spring 3422 may comprise a coil spring wrapping helically around the inner device 3402. The spring 3422 may comprise a spring mesh. The spring 3422 may be convex around the inner device 3402 or configured to bulge radially outward, within at least one portion positioned intermediately between the proximal end and distal end of the spring 3422, when in an unbiased or relaxed state, as shown in FIG. 12A.

The spring or springs 3422 may be covered or coated with an elastic membrane or film (not shown) which covers an outer and/or inner surface of the springs 3422 such that a fluid barrier is formed by the membrane circumferentially around the inner device 3402, the fluid barrier extending from the proximal sliding ring 3418 to the distal sliding ring 3418. In an unbiased configuration, the spring 3422 and the elastic membrane are compressed against an inner surface of the outer device 3404, as depicted in FIG. 12A, such that the fluid barrier forms a fluid seal around the entire circumference of the inner surface of the outer device 3404. The spring sealing feature 3416 may inhibit or prohibit distal and proximal fluid flow through or across the spring sealing feature 3416 in a fully expanded configuration.

FIG. 12B schematically illustrates the device 3400 of FIG. 12A with the spring sealing feature 3416 in an axially extended/radially compressed unsealed configuration during translational movement of the inner device 3402. As shown, in FIG. 12B, the inner device 3402 has been sufficiently translated in a proximal direction such that the ridge feature 3420 is pushing against the proximal sliding ring 3418. As the inner device 3402 is further translated in a proximal direction, the ridge 3420 causes the proximal sliding ring 3418 to slide in a proximal direction along the inner surface of the outer device 3404. As the proximal sliding ring 3418 slides in a proximal direction it exerts a force on the spring 3422 in the proximal direction. The friction between the distal sliding ring 3418 and the inner surface of the outer device 3404 resists, at least partially, the movement of the distal sliding ring 3418 along the inner surface of the outer device 3404 and can provide a counter force to the proximal force of the proximal sliding ring 3418, placing the spring 3422 in a state of tension.

Under tension, the spring 3422 may stretch in the axial direction thereby reducing its outer diameter. The outer diameter of the spring 3422 may be reduced such that the spring 3422 and/or elastic membrane no longer contacts the inner surface of the outer device 3404, at least along a portion of the circumference, and allows fluid flow across the spring sealing feature 3416. Fluid may flow between the spokes 3418*c* of the proximal and distal sliding rings 3418 to flow across the surface of the fluid barrier formed around the inner device 3402. Removing contact between the membrane-encompassed spring 3422 and the inner surface of the outer device 3402 may reduce overall friction and facilitate axial translation of the inner device 3402 relative to the outer device 3404. In some embodiments, the axial extension of the spring 3422 may reduce the compressive force of the spring sealing feature 3416 against the outer device 3404 but still maintain the spring sealing feature 3416 in contact with the outer device 3404. Reducing the compressive force may reduce friction and facilitate translation of the inner device 3402 with respect to the outer device 3404 while maintaining, at least to a degree, a fluid seal.

When the proximal force on the inner device 3402 is removed, the tension may be removed from the spring 3422 and the spring 3422 may contract bringing the proximal and distal rings 3418 closer together. The spring 3422 may expand to the inner surface of the outer device 3404 sealing device 3400, blocking fluid flow across the spring sealing feature 3416. The spring 3422 may be designed with a spring constant, such that it requires less force to deform the spring 3422 than to overcome the friction resisting sliding between the outer annulus 3418*b* and the inner surface of the outer device 3404. The spring 3422 may be configured to extend before the lagging sliding ring 3418 begins to translate, following the leading sliding ring 3418.

In some embodiments, the spring sealing feature 3416 may use two ridge features 3420, one positioned on a distal side of the distal sliding ring 3418 and one positioned on the proximal side of the proximal sliding ring 3418, in addition to or alternatively to the intermediate ridge feature 3420. Providing a transient seal that only allows fluid flow during axial translation of the inner device may significantly reduce exposure of the annular gap to proximal blood flow. Providing a transient seal that reduces friction upon axial translation of the inner device 3402 may improve the ability to readily translate the inner device 3402 while generally maintaining a fluid seal. The same tradeoff between friction that seals the annular gap and friction that inhibits smooth axial translation is not necessarily required with a dynamic seal.

Figure 13A:
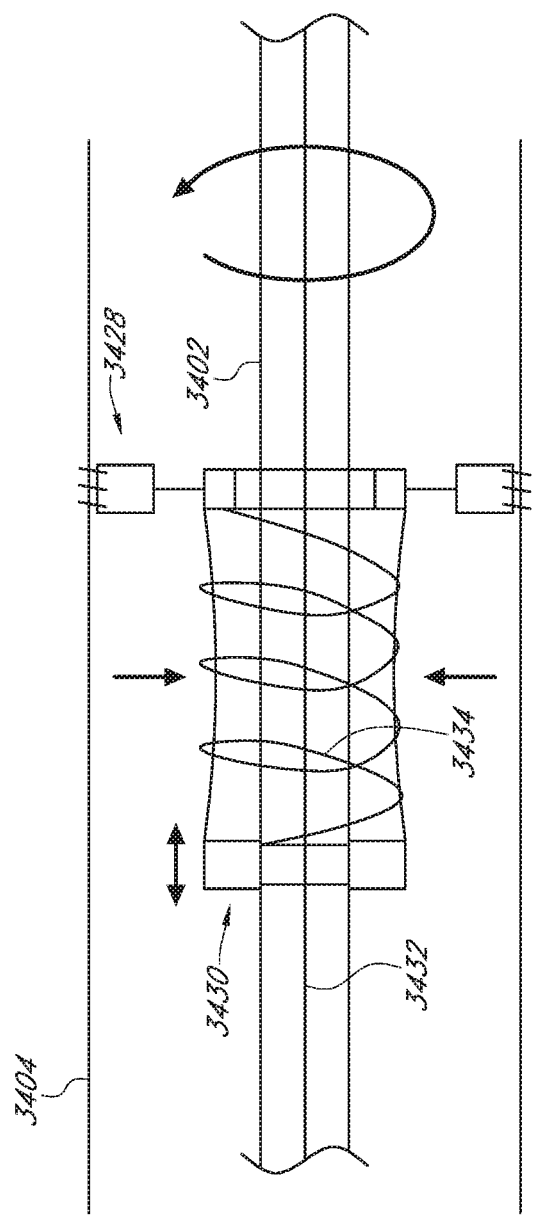
FIGS. 13A-13C schematically illustrate a device comprising a spring sealing feature in which rotation of the inner catheter axially extends and radially contracts the spring sealing mechanism.
Figure 13C:
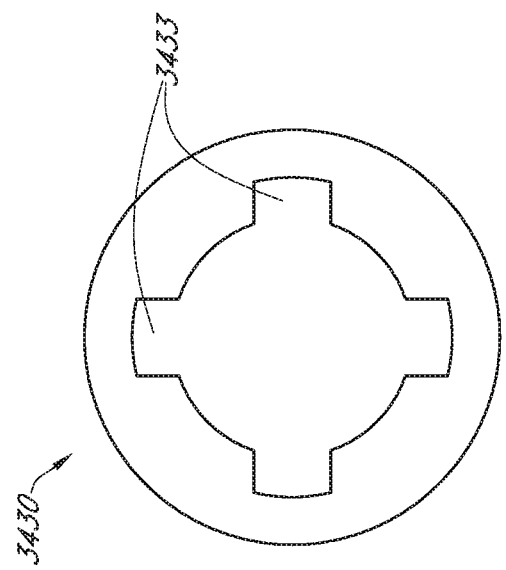
Figure 13B:
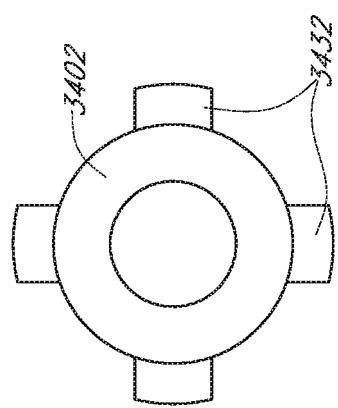

Other various configurations of the sealing feature 3406 may be dynamically responsive to movements of the inner device 3402. FIGS. 13A-13C schematically illustrate an example of a device 3400 comprising a spring sealing feature 3426 which is compressed by rotational movement of the inner device 3402 relative to the outer device 3404. FIG. 13A depicts the device 3400 in a torqued/radially compressed non-sealed configuration. FIG. 13B depicts a cross section of the inner device 3402 in FIG. 13A taken along the longitudinal axis at a point comprising a key feature 3432. FIG. 13C depicts an example of a small diameter ring 3430 used in the spring sealing feature 3426 of FIGS. 13A and 13B.

As shown in FIG. 13A, the spring sealing feature 3426 may comprise a large diameter ring 3428 and a small diameter ring 3430. The large diameter ring 3428 may be positioned proximal to the small diameter ring 3430 or vice versa. The large diameter ring 3428 may be similar to the sliding rings 3418 described elsewhere herein. However, in some embodiments, the large diameter ring 3428 may be fixed to the internal diameter of the outer device 3404, as depicted in FIG. 13A, such that the large diameter ring 3428 neither translates (e.g., slides) nor rotates with respect to the outer device 3404. The small diameter ring 3430 may extend around the circumference of the inner device and may have an outer diameter that does not extend to or near the inner surface of the outer device 3404. In some embodiments, the outer diameter of the small diameter ring 3430 may be minimized, such as to a size sufficient to couple to a torsion spring 3434.

The inner device 3402 may comprise one or more key features 3432 as illustrated in FIG. 13B. The key features 3432 may lock into the small diameter ring at particular circumferential locations. FIG. 13C depicts a small diameter ring comprising a plurality of recesses or grooves 3433, each being configured to receive one of the key features 3432 depicted in FIG. 13B. The key features 3432 may extend axially along the entire length or a portion of the length of the inner device configured to interact with the spring sealing feature 3426, as shown in FIG. 13A. The inner device 3402 may be axially translatable (e.g., slidable) within the inner diameter of the small diameter ring 3430. The key features 3432, however, may rotationally lock the small diameter ring 3430 to the inner device 3402 such that the small diameter ring 3430 rotates with the inner device 3432.

A torsion spring 3434 may extend between the large diameter ring 3428 and the small diameter ring 3430. The torsion spring 3434 may have a convex configuration around the inner device 3402 such that it extends radially outward between the large diameter ring 3428 and the small diameter ring 3430 so as to compress against the inner surface of the outer device 3404. The spring sealing device 3426 may comprise an elastic membrane or film coupled to the torsion spring 3434 to form a fluid barrier circumferentially surrounding the inner device 3402 as described elsewhere herein.

Rotation of the small diameter ring 3430 in a first direction (e.g., clockwise or counter clockwise) may cause the torsion spring 3434 to collapse such that the elastic membrane is no longer pressed into contact with the outer device 3404. The elastic membrane may form a fluid seal around the circumference of the inner surface of the outer device 3404 when compressed against the outer device 3404, similar to the spring sealing feature shown in FIG. 12A. The small diameter ring 3430 may be free to axially translate as needed along the outer surface of the inner device, such as to accommodate the radial compression of the torsion spring 3434.

Rotation of the inner device 3404 may thereby allow fluid flow across the spring sealing device 3426. The inner device 3404 may be rotated and maintained in a rotated position to allow axial translation of the inner device 3402 with respect to the outer device 3404 in order to reduce the friction between the inner device 3402 and outer device 3404. The large diameter ring 3428 may be fixed to the outer device 3404 near a distal end of the outer device 3404, maximizing the length of the annular gap that is sealed from blood exposure.

In some embodiments, the small diameter ring 3430 may be fixed to the inner device 3402 such that it is not axially translatable with respect to the inner device 3402. The small diameter ring 3430 may be an annular projection extending from the inner device 3402. The small diameter ring 3430 may be integral with the inner device 3402. The large diameter ring 3428 may be axially translatable (e.g., slidable) with respect to the inner surface of the outer device 3404. The large diameter ring 3428 may resist or prohibit rotation with respect to the inner surface of the outer device 3404. The spring constant of the torsion spring 3434 may be configured such that less torque is required to collapse the spring than to rotate the large diameter ring 3428 with respect to the outer device 3404. The large diameter ring may provide a counter force that allows the torsion spring 3434 to collapse.

In some embodiments, the large diameter ring 3428 may be mechanically prevented from rotating with respect to the outer device 3404. For example, the large diameter ring may comprise key features and the inner surface of the outer device 3404 may comprises corresponding recesses or grooves, as described elsewhere herein or vice versa. In some embodiments, the torsion spring 3434 and/or the elastic membrane may extend from the small diameter ring to an outer annulus of the large diameter ring 3428 or some circumference between an inner diameter and outer diameter of the large diameter ring 3428. Rotation of the inner device 3402 may collapse the torsion spring 3434 to allow fluid flow and/or reduce friction between the inner device 3402 and outer device 3404 as described with respect to FIGS. 13A-13C. However, the spring sealing feature 3426 may be axially translatable with respect to the outer device 3404 such that it may move along with the inner device 3402.

Disclosed herein are various embodiments for sealing an annular gap between vascular device such as device 3400, described elsewhere herein, and a body vessel such as a blood vessel (e.g., a neurovascular artery). Sealing a blood vessel around a catheter device, particularly a catheter configured for the removal (e.g., aspiration) of a blood clot may advantageously prevent blood flow from carrying a clot or fragment of a clot, such as a clot captured on a distal end of the catheter, further downstream. For example, for a device positioned upstream of the clot, such as in a neurovascular artery, the seal between the device and the blood vessel may prevent antegrade blood flow from dislodging a captured blood clot from a distal end of the device and carrying it downstream, which could result in an embolism in a downstream location.

Figure 14:
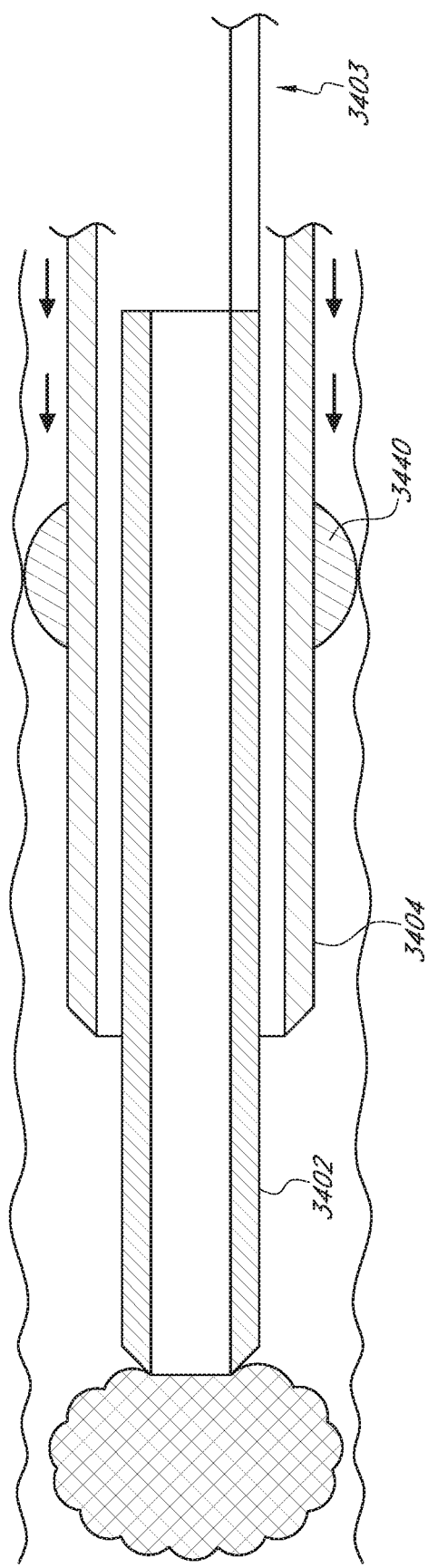
FIG. 14 schematically illustrates a catheter device comprising a vessel sealing feature configured to fluidly seal the gap between the outer diameter of the catheter and the blood vessel or other body lumen the device is inserted within.

The device 3400 may comprise a vessel sealing feature 3440 positioned on an outer surface of the device 3400 (e.g., on an outer surface of the outer access catheter device 3404). FIG. 14 schematically illustrates an example of a device 3400 comprising a vessel sealing feature 3440. The vessel sealing feature 3440 may be annular and may extend around the entire circumference of the device 3400. The vessel sealing feature 3440 may be positioned at a distal end of the device 3400, near a proximal end of the device 3400, or somewhere intermediate the distal end and proximal end. The vessel sealing feature 3440 may be passive comprising a static structure that seals the vessel or it may be active comprising a dynamic structure that is activated and/or deactivate to transition between a sealing state and a non-sealing state.

The vessel sealing feature 3440 may comprise the same or similar features as protrusion 3408 configured to extend around the outer surface of the inner device 3402, except that it is configured to extend around the outer surface of the outer device 3404. The vessel sealing feature 3440 may form an expanded diameter portion of the device 3400 (or at least of a portion of the device inserted into the vasculature to be occluded by the vessel sealing feature 3440). The vessel sealing feature 3440 may be extremely compliant such that it may have a diameter large enough to seal a blood vessel of an unknown or variable diameter while being soft and deformable enough to be compressed and placed contact with the blood vessel wall without damaging (e.g., rupturing or tearing) the blood vessel wall or intima.

The vessel sealing feature 3440 may be formed as a part of an outer jacket as described elsewhere herein. The vessel sealing feature 3440 may comprise a soft elastomeric polymer. The vessel sealing feature 3440 may be formed from a same or different material as the device 3400 (e.g., the outer jacket of the device). The vessel sealing feature 3440 may be a separate component which is coupled to the device 3400. For example, the vessel sealing feature 3440 may be a preformed ring, similar to a wide O-ring, which is placed over the outer surface of the device 3400. The device 3400 may be configured with a circumferential recess or groove configured to receive the vessel sealing feature 3440. The vessel sealing feature 3440 may have an inner diameter that is smaller, in an unbiased state, than the outer diameter of the device 3400 (or the recessed diameter of the groove). The vessel sealing feature 3440 may need to be at least partially expanded (e.g., stretched) in order to position the vessel sealing feature 3440 over the device 3400 and the compressive elastic force of the vessel sealing feature 3440 may frictionally secure the vessel sealing feature 3440 to the device 3400.

In some embodiments, the vessel sealing feature 3440 may be additionally or alternatively secured to the device by melting or molding the sealing feature onto the device 3400 or using an adhesive (e.g., a biocompatible adhesive). In some embodiments, the vessel sealing feature 3400 may be softer and more flexible or compliant along an outer diameter than along an inner diameter. In some embodiments, the vessel sealing feature 3400 may be thinner along an outer diameter than along an inner diameter. In some implementations, the vessel sealing feature 3440 may be custom-formed in size and/or shape to the anatomy of a particular vessel. The anatomy may be patient-specific. In some embodiments, the vessel sealing feature 3440 is interchangeable such that a custom or otherwise specifically shaped and/or sized vessel sealing feature 3440 may be replaceably attached to the device 3400. In some embodiments, the vessel sealing feature 3440 may be a soft hydrogel. The hydrogel may be configured to swell nominally or not at all in situ.

In some embodiments, the vessel sealing feature 3440 may be active. The vessel sealing feature 3440 may comprise the same or similar features as the expandable bulge 3410 described elsewhere herein. For example, the vessel sealing feature 3440 may comprise a light-sensitive or electrosensitive material, such as a light-sensitive hydrogel and/or an electrosensitive hydrogel. An electric current or light may be passed through an insulator or fiber optic cable to the hydrogel or other active material. The hydrogel may expand upon the application of light and/or an electric current and may collapse upon removal of the stimuli or vice-versa.

A hydrogel may be configured to swell to a controlled or expected volume when exposed to the physiological environment in situ. For example, the hydrogel may be configured to swell in response to body temperature, blood exposure, and/or interaction with a physiological factor, such as an enzyme. In some implementations, the amount of swelling may be controlled by a parameter of the stimulus (e.g, the amount of current or intensity of the light).

In some embodiments, the vessel sealing feature 3440 may be inflatable via pressurized fluid (e.g. a gas or liquid, such as saline) which serves to inflate the vessel sealing feature 3440 such as an inflatable balloon. The vessel sealing feature 3440 may be inflated and deflated to a controllable extent by controlling the pressure applied to the inflating fluid. In some embodiments, the vessel sealing feature 3440 may be configured to be in-line or flush with the outer diameter of the device 3400 in an inactivated state. In other embodiments, the vessel sealing feature 3440 may extend slightly beyond the outer diameter of the device 3400 in an inactivate state, but not to the extent that it seals the blood vessel or comes into significantly increased contact with the blood vessel creating additional friction.

Any of the catheter shaft or sections of the catheter shaft or telescoping extensions in accordance with the present invention, such as inner device 3402 or outer device 3404, may comprise a multi-layer construct having a high degree of flexibility and sufficient push ability to reach deep into the cerebral vasculature, such as at least as deep as the petrous, cavernous, or cerebral segment of the internal carotid artery (ICA).

Figure 15:
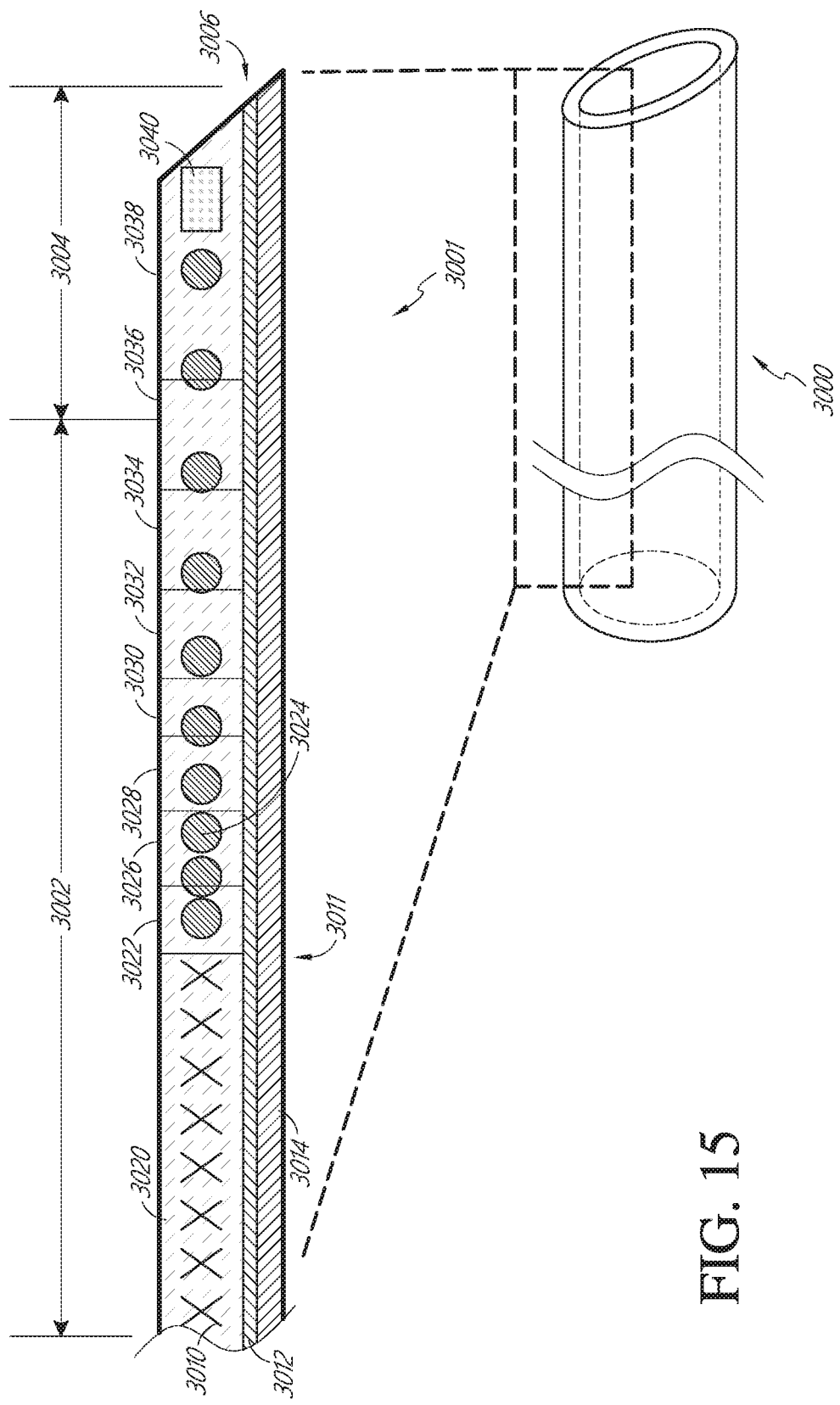
FIG. 15 illustrates a cross-sectional elevational view of a catheter wall according to an embodiment.

In one example, referring to FIG. 15, a catheter 3000, which may be the same or similar to device 3400, may have an effective length from the manifold to distal tip from about 70 cm to about 150 cm, from about 80 cm to about 140 cm, from about 90 cm to about 130 cm, from about 100 cm to about 120 cm, or from about 105 cm to about 115 cm. The outer diameter of the catheter 3000 may be from about 0.07 inches to about 0.15 inches, from about 0.08 inches to about 0.14 inches, from about 0.09 inches to about 0.13 inches, from about 0.1 inches to about 0.12 inches, or from about 0.105 inches to about 0.115 inches, and may be lower in a distal segment than in a proximal segment. The inner diameter 3108 of the catheter 3000 in a single central lumen embodiment may be greater than or equal to about 0.11 inches, greater than or equal to about 0.1 inches, greater than or equal to about 0.09 inches, greater than or equal to about 0.088 inches, greater than or equal to about 0.08 inches, greater than or equal to about 0.07 inches, greater than or equal to about 0.06 inches, or greater than or equal to about 0.05 inches. The inner diameter 3108 of the catheter 3000 in a single central lumen embodiment may be less than or equal to about 0.11 inches, less than or equal to about 0.1 inches, less than or equal to about 0.09 inches, less than or equal to about 0.088 inches, less than or equal to about 0.08 inches, less than or equal to about 0.07 inches, less than or equal to about 0.06 inches, or less than or equal to about 0.05 inches. Referring to FIG. 15, an inner liner 3014 may be formed by dip coating a mandrel (not shown) to provide a thin walled tubular inside layer of the catheter body 3000. The dip coating may be produced by coating a wire such as a silver coated copper wire in PTFE. The mandrel may thereafter be axially elongated to reduce diameter, and removed to leave the tubular inner liner. The outside surface of the tubular inner liner 3014 may thereafter be coated with a soft tie layer 3012 such as polyurethane (e.g., Tecoflex™), to produce a layer having a thickness of no more than about 0.005 inches, and in some implementations approximately 0.001 inches. The tie layer 3012 will generally extend along at least about the most distal 10 cm or 20 cm of the catheter shaft 3000 generally less than about 50 cm and may in one implementation extend approximately the distal 30 cm of the catheter shaft 3000, 3100.

A braid such as a 75 ppi stainless steel braid 3010 may thereafter be wrapped around the inner liner 3014 through a proximal zone up to a distal transition 3011. From the distal transition 3011 to the distal end of the catheter 3000, a coil 3024 comprising a shape memory material such as a Nitinol alloy may thereafter be wrapped around the inner liner 3014. In one implementation, the Nitinol coil has a transition temperature below body temperature so that the Nitinol resides in the austinite (springy) state at body temperature. Adjacent loops or filars of the coil 3024 may be closely tightly wound in a proximal zone with a distal section having looser spacing between adjacent loops. In an embodiment having a coil section 3024 with an axial length of at least between about 20% and 30% of the overall catheter length, (e.g., 28 cm coil length in a 110 cm catheter shaft 3000), at least the distal 1 or 2 or 3 or 4 cm of the coil will have a spacing that is at least about 130%, and in some implementations at least about 150% or more than the spacing in the proximal coil section. In a 110 cm catheter shaft 3000 having a Nitinol coil the spacing in the proximal coil may be about 0.004 inches and in the distal section may be at least about 0.006 inches or 0.007 inches or more. In embodiments comprising an extension catheter, the distal extendable section of the catheter may be constructed according to the foregoing. The length of the coil 3024 may be proportioned to the length of the extendable catheter segment or the total (e.g., extended) length of the catheter 3000. The coil 3024 may extend from a distal end of the extendable segment over at least about 50%, 60%, 70%, 80%, or 90% of the length of the extendable segment. In some embodiments, the catheter 3000 or the extendable segment may not comprise a braid and the coil 3024 may extend to the proximal end of the extendable segment (100% of the length). [0082] The distal end of the coil 3024 can be spaced proximally from the distal end of the inner liner 3014, for example, to provide room for an annular radiopaque marker 3040. The coil 3024 may be set back proximally from the distal end, in some embodiments, by approximately no more than 1 cm, 2 cm, or 3 cm. In one embodiment, the distal end of the catheter 3000 is provided with a beveled distal surface 3006 residing on a plane having an angle of at least about 10° or 20° and in one embodiment about 30° with respect to a longitudinal axis of the catheter 3000. The radiopaque marker 3040 may reside in a plane that is transverse to the longitudinal axis. Alternatively, at least the distally facing edge of the annular radiopaque marker 3040 may be an ellipse, residing on a plane which is inclined with respect to the longitudinal axis to complement the bevel angle of the distal surface 3006.

After applying the proximal braid 3010, the distal coil 3024 and the RO marker 3040 an outer Jacket 3020 maybe applied such as a shrink wrap tube to enclose the catheter body 3000. The outer shrink-wrapped sleeve 3020 may comprise any of a variety of materials, such as polyethylene, polyurethane, polyether block amide (e.g., PEBAX™), nylon or others known in the art. Sufficient heat is applied to cause the polymer to flow into and embed the proximal braid and distal coil.

In one implementation, the outer shrink wrap jacket 3020 is formed by sequentially advancing a plurality of short tubular segments 3022, 3026, 3028, 3030, 3032, 3034, 3036, 3038 concentrically over the catheter shaft subassembly, and applying heat to shrink the sections on to the catheter 3000 and provide a smooth continuous outer tubular body. The foregoing construction may extend along at least the most distal 10 cm, and preferably at least about the most distal 20 cm, 25 cm, 30 cm, 35 cm, 40 cm, or more than 40 cm of the catheter body 3000. The entire length of the outer shrink wrap jacket 3020 may be formed from tubular segments and the length of the distal tubular segments (e.g., 3022, 3026, 3028, 3030, 3032, 3034, 3036, 3038) may be shorter than the one or more tubular segments forming the proximal portion of the outer shrink wrap jacket 3020 in order to provide steeper transitions in flexibility toward the distal end of the catheter 3000.

The durometer of the outer wall segments may decrease in a distal direction. For example, proximal segments such as 3022 and 3026, may have a durometer of at least about 60 or 70D, with gradual decrease in durometer of successive segments in a distal direction to a durometer of no more than about 35D or 25D or lower. A 25 cm section may have at least about 3 or 5 or 7 or more segments and the catheter 3000 overall may have at least about 6 or 8 or 10 or more distinct flexibility zones. The distal 1 or 2 or 4 or more segments 3036, 3038, may have a smaller OD following shrinking than the more proximal segments 3022-3034 to produce a step down in OD for the finished catheter body 3000. The length of the lower OD section 3004 may be within the range of from about 3 cm to about 15 cm and in some embodiments is within the range of from about 5 cm to about 10 cm such as about 7 or 8 cm, and may be accomplished by providing the distal segments 3036, 3038 with a lower wall thickness.

Referring to FIGS. 16A-16B, there is illustrated one example of an outer jacket segment stacking pattern for a progressive flexibility catheter of the type discussed in connection with FIG. 15. A distal segment 3038 may have a length within the range of about 1-3 cm, and a durometer of less than about 35D or 30D. An adjacent proximal segment 3036 may have a length within the range of about 4-6 cm, and a durometer of less than about 35D or 30D. An adjacent proximal segment 3034 may have a length within the range of about 4-6 cm, and a durometer of about 35D or less. An adjacent proximal segment 3032 may have a length within the range of about 1-3 cm, and a durometer within the range of from about 35D to about 45D (e.g., 40D). An adjacent proximal segment 3030 may have a length within the range of about 1-3 cm, and a durometer within the range of from about 50D to about 60D (e.g., about 55D). An adjacent proximal segment 3028 may have a length within the range of about 1-3 cm, and a durometer within the range of from about 35D to about 50D to about 60D (e.g., about 55D). An adjacent proximal segment 3026 may have a length within the range of about 1-3 cm, and a durometer of at least about 60D and typically less than about 75D. More proximal segments may have a durometer of at least about 65D or 70D. The distal most two or three segments may comprise a material such as Tecothane, and more proximal segments may comprise PEBAX or other catheter jacket materials known in the art. At least three or five or seven or nine or more discrete segments may be utilized, having a change in durometer between highest and lowest along the length of the catheter shaft of at least about 10D, preferably at least about 20D and in some implementations at least about 30D or 40D or more.

In another embodiment, the most distal portion of the catheter 3000 may comprise a durometer of less than approximately 35D (e.g., 25D) to form a highly flexible distal portion of the catheter and have a length between approximately 25 cm and approximately 35 cm. In other embodiments, the length may be between approximately 15 cm and approximately 25 cm. The distal portion may comprise one or more tubular segments of the same durometer (e.g., segment 3038) or of different durometers. In some embodiments, one or more of the distal most segments may comprise a polyether-based thermoplastic polyurethane (e.g., Tecothane®). More proximal segments may comprise a polyether block amide (e.g., PEBAX®). A series of proximally adjacent tubular segments to the distal portion may form a transition region between a proximal stiffer portion of the catheter 3000 and the distal highly flexible portion of the catheter. The series of tubular segments forming the transition region may have the same or substantially similar lengths, such as approximately 1 cm. The relatively short length of the series of tubular segments may provide a steep drop in durometer over the transition region. For example, the transition region may have a proximal tubular segment 3036 (proximally adjacent the distal portion) having a durometer of approximately 35D. An adjacent proximal segment 3034 may have a durometer of approximately 55D. An adjacent proximal segment 3032 may have a durometer of approximately 63D. An adjacent proximal segment 3030 may have a durometer of approximately 72D. One or more of the segments within the transition region may comprise a length between about 1 and 4 cm. For example, the transition region may comprise a proximal segment 3036 approximately 4 cm and 35D, an adjacent segment 3034 approximately 3 cm and 37D, an adjacent segment 3032 approximately 1 cm and 47D, an adjacent segment 3030 approximately 1 cm and 55D, an adjacent segment 3028 approximately 1 cm and 63D, and an adjacent segment 3026 approximately 1 cm and 72D. In some embodiments, the length of the distal portion of the catheter 3000, including the highly flexible distal portion and the transition region, may be between about 25-30 cm, between about 30-35 cm, between about 35 to 40 cm, or between about 40-45 cm. More proximal segments may comprise a durometer or durometers greater than approximately 72D and may extend to the proximal end of the catheter or extension catheter segment. For instance, an extension catheter segment may comprise a proximal portion greater than approximately 72D between about 1 cm and about 3 cm. In some embodiments, the proximal portion may be about 2 cm long. In some embodiments, the most distal segments (e.g., 3038-3030) or at least the transition region may comprise PEBAX® and more proximal segments may comprise a generally stiffer material, such as Vestamid®.

The inner diameter of the catheter 3000 or catheter extension segment may be between approximately 0.06 and 0.08 inches, between approximately 0.065 and 0.075 inches, or between 0.068 and 0.073 inches. In some embodiments, the inner diameter is approximately 0.071 inches. In some embodiments, the distal most portion may taper to a decreased inner diameter as described elsewhere herein. The taper may occur approximately between the distal highly flexible portion and the transition region (e.g., over the most proximal portion of the distal highly flexible portion). The taper may be relatively gradual (e.g., occurring over approximately 10 or more cm) or may be relatively steep (e.g., occurring over less than approximately 5 cm). The inner diameter may taper to an inner diameter between about 0.03 and 0.06 inches. For example, the inner diameter may be about 0.035 inches, about 0.045 inches, or about 0.055 inches at the distal end of the catheter 3000. In some embodiments, the inner diameter may remain constant, at least over the catheter extension segment. In some embodiments, the coil 3024 may extend from a distal end of the catheter 3000 along the highly flexible distal portion ending at the distal end of the transition region. In other embodiments, the coil 3024 may extend from a distal end of the catheter to the proximal end of the transition region, to a point along the transition region, or proximally beyond the transition region. In other embodiments, the coil 3024 may extend the entire length of the catheter 3000 or catheter extension segment as described elsewhere herein. The braid 3010, when present, may extend from the proximal end of the coil 3024 to the proximal end of the catheter 3000 or catheter extension segment.

The catheters of the present invention may be composed of any of a variety of biologically compatible polymeric resins having suitable characteristics when formed into the tubular catheter body segments. Exemplary materials include polyvinyl chloride, polyethers, polyamides, polyethylenes, polyurethanes, copolymers thereof, and the like. In one embodiment, both the proximal body segment 33 and distal body segment 34 will comprise a polyvinyl chloride (PVC), with the proximal body segment being formed from a relatively rigid PVC and the distal body segment being formed from a relatively flexible, supple PVC. Optionally, the proximal body segment may be reinforced with a metal or polymeric braid or other conventional reinforcing layer.

Although the present invention has been described in terms of certain preferred embodiments, it may be incorporated into other embodiments by persons of skill in the art in view of the disclosure herein. The scope of the invention is therefore not intended to be limited by the specific embodiments disclosed herein, but is intended to be defined by the full scope of the following claims.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc.

Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A sealed neurovascular extendable catheter comprising:
an outer catheter having a proximal end and a distal end;
an inner catheter having a proximal end and a distal end and being extendable through the outer catheter such that the distal end of the inner catheter is configured to extend beyond the distal end of the outer catheter; and
a seal positioned between the inner catheter and the outer catheter, the seal being configured to fluidly seal at least a portion of an annular gap formed between an outer surface of the inner catheter and an inner surface of the outer catheter, the seal comprising:
- a proximalmost edge,
- a distalmost edge comprising a trailing point and a leading point being displaced axially distally relative to the trailing point,
- a thickness configured to allow axial translation of the inner catheter relative to the outer catheter, and
- at least one annular protrusion extending around a circumference of the inner catheter, the at least one annular protrusion comprising a chevron-shaped protrusion pointing in a distal direction, wherein at least one of the proximalmost edge or the distalmost edge is elliptical, and wherein the proximalmost edge is generally parallel to the distalmost edge.

2. The sealed neurovascular extendable catheter of claim 1, wherein the at least one annular protrusion is compliant and comprises an outer diameter which when unconstrained is slightly larger than an inner diameter of the outer catheter.

3. The sealed neurovascular extendable catheter of claim 1, wherein the distalmost edge lies on a plane that is inclined relative to a longitudinal axis of the inner catheter.

4. The sealed neurovascular extendable catheter of claim 3, wherein the plane resides at an angle within a range of from about 20 to about 50 degrees from the longitudinal axis.

5. The sealed neurovascular extendable catheter of claim 1, wherein the proximalmost edge and the distalmost edge are elliptical.

6. The sealed neurovascular extendable catheter of claim 1, wherein at least one of the proximalmost edge or the distalmost edge is positioned at a non-orthogonal angle relative to a longitudinal axis of the inner catheter.

7. The sealed neurovascular extendable catheter of claim 6, wherein the proximalmost edge and the distalmost edge are positioned at non-orthogonal angles relative to the longitudinal axis of the inner catheter.

8. A sealed neurovascular extendable catheter comprising:
an outer catheter having a proximal end and a distal end;
an inner catheter having a proximal end and a distal end and being extendable through the outer catheter such that the distal end of the inner catheter is configured to extend beyond the distal end of the outer catheter; and
a seal positioned between the inner catheter and the outer catheter, the seal being configured to fluidly seal at least a portion of an annular gap formed between an outer surface of the inner catheter and an inner surface of the outer catheter, the seal comprising:
- a proximalmost edge comprising a proximal trailing point and a proximal leading point, the proximal leading point being displaced axially distally relative to the proximal trailing point,
- a distalmost edge comprising a distal trailing point and a distal leading point, the distal leading point being displaced axially distally relative to the distal trailing point, the distal trailing point being displaced axially proximally relative to the proximal leading point, and
- a thickness configured to allow axial translation of the inner catheter relative to the outer catheter, and
- at least one annular protrusion extending around a circumference of the inner catheter, the at least one annular protrusion comprises a chevron-shaped protrusion pointing in a distal direction, wherein at least one of the proximalmost edge or the distalmost edge is elliptical.

9. The sealed neurovascular extendable catheter of claim 8, wherein the at least one annular protrusion is compliant and comprises an outer diameter which when unconstrained is slightly larger than an inner diameter of the outer catheter.

10. The sealed neurovascular extendable catheter of claim 8, wherein the distalmost edge lies on a plane that is inclined relative to a longitudinal axis of the inner catheter.

11. The sealed neurovascular extendable catheter of claim 10, wherein the plane resides at an angle within a range of from about 20 to about 50 degrees from the longitudinal axis.

12. The sealed neurovascular extendable catheter of claim 8, wherein the proximalmost edge and the distalmost edge are elliptical.

13. The sealed neurovascular extendable catheter of claim 8, wherein the proximalmost edge is generally parallel to the distalmost edge.

14. The sealed neurovascular extendable catheter of claim 8, wherein at least one of the proximalmost edge or the distalmost edge is positioned at a non-orthogonal angle relative to a longitudinal axis of the inner catheter.

15. The sealed neurovascular extendable catheter of claim 14, wherein the proximalmost edge and the distalmost edge are positioned at non-orthogonal angles relative to the longitudinal axis of the inner catheter.

* * * * *